(12) United States Patent
Dunki-Jacobs et al.

(10) Patent No.: US 10,507,285 B2
(45) Date of Patent: Dec. 17, 2019

(54) PRESSURIZED GAS POWERED MEDICAMENT TRANSFER AND RE-SUSPENSION APPARATUS AND METHOD

(71) Applicant: Enable Injections, Inc., Cincinnati, OH (US)

(72) Inventors: Adam Dunki-Jacobs, Cincinnati, OH (US); Michael D. Hooven, Cincinnati, OH (US); Matthew J. Huddleston, Loveland, OH (US); Richard P. Nuchols, Williamsburg, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 0 days.

(21) Appl. No.: 15/561,820

(22) PCT Filed: Mar. 24, 2016

(86) PCT No.: PCT/US2016/023973
§ 371 (c)(1),
(2) Date: Sep. 26, 2017

(87) PCT Pub. No.: WO2016/154413
PCT Pub. Date: Sep. 29, 2016

(65) Prior Publication Data
US 2018/0110922 A1    Apr. 26, 2018

Related U.S. Application Data

(60) Provisional application No. 62/138,762, filed on Mar. 26, 2015.

(51) Int. Cl.
*A61M 5/178* (2006.01)
*A61J 1/20* (2006.01)
(Continued)

(52) U.S. Cl.
CPC ............ *A61M 5/1782* (2013.01); *A61J 1/20* (2013.01); *A61J 1/2006* (2015.05); *A61J 1/2075* (2015.05);
(Continued)

(58) Field of Classification Search
CPC .......... A61J 1/20; A61J 1/2006; A61J 1/2089; A61J 1/2096; A61J 1/1406; A61J 1/201;
(Continued)

(56) References Cited

U.S. PATENT DOCUMENTS 3,115,133 A * 12/1963 Morando ................ A61M 5/30
604/70
4,906,260 A    3/1990 Emheiser et al.
(Continued)

FOREIGN PATENT DOCUMENTS

EP    2221076 A1    8/2010
JP    2013500773 A1   1/2013
(Continued)

OTHER PUBLICATIONS

International Search Report dated Jul. 1, 2016 for International Application No. PCT/US2016/023973 from the Korean Intellectual Property Office.
(Continued)

*Primary Examiner* — Bhisma Mehta
*Assistant Examiner* — Larry R. Wilson
(74) *Attorney, Agent, or Firm* — Cook Alex Ltd.; R. Blake Johnston

(57) ABSTRACT

Apparatus and method are described employing pressurized gas to transfer, mix and/or reconstitute medicament con-
(Continued)

tained in a vial and flowing it into an injection device. Pressurized gas may be provided by prefilled cartridge.

6 Claims, 16 Drawing Sheets

(51) Int. Cl.
*A61M 5/152* (2006.01)
*A61M 5/20* (2006.01)
*A61M 5/00* (2006.01)
*A61M 5/148* (2006.01)
*A61M 5/19* (2006.01)
*A61M 5/24* (2006.01)

(52) U.S. Cl.
CPC ............ *A61J 1/2082* (2015.05); *A61J 1/2089* (2013.01); *A61M 5/002* (2013.01); *A61M 5/148* (2013.01); *A61M 5/152* (2013.01); *A61M 5/178* (2013.01); *A61M 5/19* (2013.01); *A61M 5/20* (2013.01); *A61M 5/2046* (2013.01); *A61M 5/2053* (2013.01); *A61M 5/2425* (2013.01); *A61J 1/2096* (2013.01); *A61M 2205/58* (2013.01)

(58) Field of Classification Search
CPC .... A61J 1/2075; A61J 1/2082; A61M 5/1483; A61M 5/155; A61M 5/2046; A61M 5/2053; A61M 5/30; A61M 5/3015; A61M 5/002; A61M 5/178; A61M 5/1782; A61M 5/19; A61M 5/2425; A61M 5/2455; A61M 5/2459; A61M 5/2466; A61M 2005/247; A61M 2005/2474; A61M 2005/3114; A61M 2005/3115; A61M 2205/8218; A61M 2205/8225

See application file for complete search history.

(56) References Cited

U.S. PATENT DOCUMENTS

| | | | |
|---|---|---|---|
| 6,364,865 B1 * | 4/2002 | Lavi | A61J 1/2089 604/411 |
| 6,374,876 B2 | 4/2002 | Bynum | |
| 6,478,771 B1 * | 11/2002 | Lavi | A61J 1/2089 604/506 |
| 6,689,093 B2 * | 2/2004 | Landau | A61M 5/30 604/143 |
| 8,323,237 B2 | 12/2012 | Radmer et al. | |
| 2002/0004643 A1 | 1/2002 | Carmel et al. | |
| 2004/0254525 A1 | 12/2004 | Uber et al. | |
| 2009/0204066 A1 | 8/2009 | Radmer et al. | |
| 2011/0220116 A1 | 9/2011 | Lowenstein et al. | |
| 2012/0123382 A1 | 5/2012 | Kubo | |
| 2013/0296807 A1 | 11/2013 | Lintern et al. | |

FOREIGN PATENT DOCUMENTS

| | | |
|---|---|---|
| WO | WO01/72354 A2 | 10/2001 |
| WO | WO2008/153460 A1 | 12/2008 |
| WO | WO 2014/204894 | 12/2014 |

OTHER PUBLICATIONS

Written Opinion of the Korean International Searching Authority dated Jun. 21, 2016 for International Application No. PCT/US2016/023973.

Austrailian Examination Report No. 1 dated Dec. 1, 2017 from Australian Patent Applicaiton No. 2016235138.

European Patent Office, Partial supplementary European search report, counterpart EP Appl. No. 16769673, dated May 15, 2018.

International Search and Written Report from the International Search Authority for PCT App. No. PCT/US2018/056130, dated Feb. 13, 2019 (14 pages).

\* cited by examiner

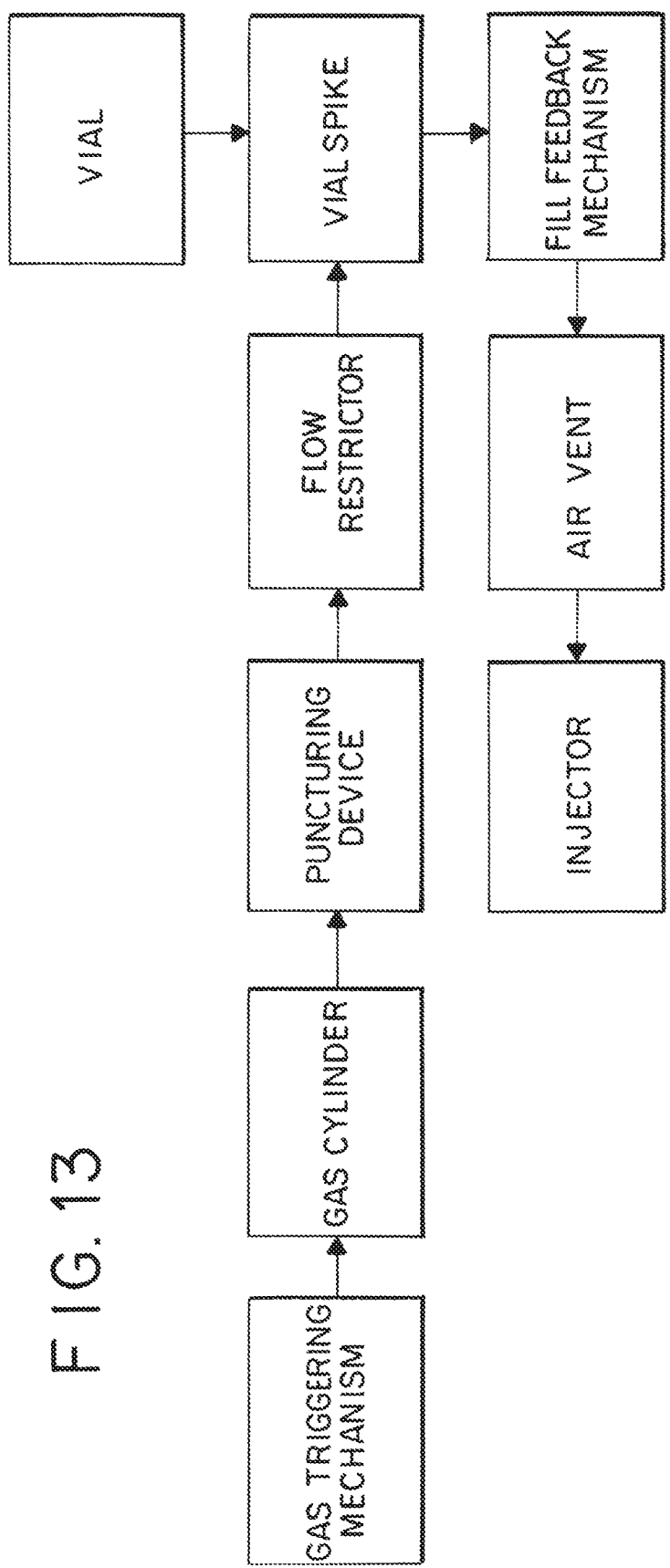
F I G. 13

F.I.G. 21

PRESSURIZED GAS POWERED MEDICAMENT TRANSFER AND RE-SUSPENSION APPARATUS AND METHOD

This application claims priority to and the benefit of U.S. Provisional Application No. 62/138,762, filed Mar. 26, 2015.

The present subject matter relates generally to apparatus and methods for transferring and/or mixing medicaments in liquid or un-reconstituted form in a vial.

BACKGROUND

Drugs, biologics, vaccines, antibiotics and other medical materials ("medicaments") intended for injection into a subject are commonly supplied in sealed vials from which the medicament must be withdrawn prior to injection and transferred to an injection device. In some cases the medicament is in liquid form, and in other cases it is in a dry or powder form, such as lyophilized form, and must be reconstituted or re-suspended with a liquid diluent before it can be withdrawn from the vial. In this description, "re-suspend" is used in a comprehensive sense to include reconstitute and dilute.

Devices for transferring and/or re-suspending medicaments supplied in vials have been the subject of significant development, as have injection devices for injecting a medicament into a subject. Examples of both are set forth in PCT International Application No. PCT/US2014/042627, entitled Vial Transfer and Injection Apparatus and Method, which published as PCT Publication No. WO2014204894, on Dec. 24, 2014, and is hereby incorporated by reference in its entirety. Various embodiments of transfer and mixing or re-suspending devices and injection devices are disclosed in detail therein. The transfer and re-suspending devices shown there employ spring-loaded pistons and cylinders for transferring the medicament and/or diluent and/or re-suspended medicament as between the vial or vials and injection device. While these devices work well, further cost and/or size reduction and/or simplification continue to be desirable.

SUMMARY

In accordance with one aspect of the present subject matter, pressurized gas from a source is employed to transfer, mix and/or reconstitute medicament contained in a vial. The pressurized gas source may be, for example, a pressure vessel such as but not limited to a pre-filled pressurized gas cartridge or cylinder. More specifically, in one aspect, a method of transferring fluid from a fluid-containing vial to an injection device is provided. The method may include introducing pressurized gas from a pressure vessel into a vial; flowing fluid from the vial under pressure from the gas; and flowing the fluid from the vial into an injection device under the force of the pressurized gas.

In a further aspect, two or more vials may be used and fluid from a first vial flowed into a second vial to combine or mix with the contents of the second vial and the combined fluid flowed into an injection device or into one or more additional vials and into an injection device. To reconstitute a lyophilized drug the first vial may contain a liquid diluent and the second vial contain the drug. To dilute a liquid medicament, the first or second vial may contain a diluent and the other vial contain a liquid medicament. To provide a drug mixture or "cocktail" each vial may contain a liquid medicament. There may be other variations or combinations, and additional vials employed. The common feature is the use of pressurized gas, such as from a pre-filled pressurized gas cylinder or cartridge, to provide energy or force to move the fluids from vial to vial and into an injection device.

The injection device may include an expandable reservoir, and the resultant fluid, such as combined diluent and medicament or combined liquid medicaments flowed into the expandable reservoir under pressure from the pressurized gas. The pressure may optionally cause the reservoir to expand as it fills with the fluid or the combined diluent and medicament, in effect, charging the injection device for subsequent use by medical personnel or the subject themselves.

In another aspect of the present disclosure, a medicament transfer apparatus is disclosed for transferring fluid from a fluid-containing vial to an injection device including medicament reservoir. The apparatus includes a pressurized gas source, such as but not limited to a pressure vessel such as a pre-filled pressurized gas cartridge or cylinder, at least one vial receiving station, and a medication injection device receiving station. A gas flow path is communicable between the gas source and the vial receiving station and a fluid flow path communicable between the vial receiving station and the medication injection device receiving station.

The medicament transfer apparatus may have more than one vial receiving station and may include, for example, a first vial receiving station and a second vial receiving station, or more. A gas flow path is communicable between the pressurized gas source and the first vial receiving station receiving a vial containing a liquid such as a diluent or liquid medicament. The second and other vial receiving stations may be configured to receive vials containing any suitable contents, such as a lyophilized drug that is to be reconstituted by a diluent, a liquid medicament to be diluted by a diluent or mixed with another liquid medicament or variations of these. A fluid flow path is communicable from one vial receiving station to another to allow the desired fluid flow of diluent, medicament or combination. The fluid flow path also communicates between the vials and the injection device receiving station so that the resultant fluid, whether a reconstituted lyophilized drug, diluted medicament or liquid medicament mixture, may be flowed into an injection device. The motive energy or force for the transfer of fluid between the vials and to the injection device receiving station is the pressurized gas from the pressurized gas source.

The medicament transfer apparatus may also include an injection device removably secured to the device receiving station. The injection device may include a reservoir such as one that is expandable under pressure of fluid from the force of the pressurized gas.

In accordance with another aspect of this disclosure, another re-suspension device is disclosed for re-suspending the medicament contents (such as a micro-aggregate) of a vial of the type having an open end sealed by a septum. This re-suspension device comprises a housing that includes a diluent port, a gas port, a vent port, and a vial receiving station. It also includes a first spike lumen and a second spike lumen extending from the vial receiving station for piercing a vial septum when a vial is received at the vial receiving station. A gas flow path in the housing communicates between the gas entry port and the first spike lumen; a diluent flow path communicates between the diluent port and the first spike lumen; and a vent flow path communicates between the vent port and the second spike lumen. A hydrophobic filter is cooperatively associated with the vent flow path for filtering gas passing the vent flow path and substantially preventing the escape of liquid from the vent flow path.

In connection with this aspect, a method of re-suspending medicament contents of a vial is also provided. The method comprises: introducing diluent into the vial; injecting gas under pressure into the vial below the level of the diluent in the vial to cause agitation of the diluent and medicament; venting gas from the vial; and continuing the injecting and venting until the medical contents are substantially re-suspended.

BRIEF DESCRIPTION OF DRAWINGS

The above aspects of the present subject matter and many other aspects are disclosed in following description of the non-exclusive examples shown in the attached drawings, of which:

Specifically, FIG. 1 is a perspective view of a single-vial system including the single vial holder, transfer apparatus and injection device system embodying the present subject matter.

FIG. 2 is a perspective view of a dual vial system including the dual vial holder, transfer apparatus and injection device system embodying the present subject matter.

FIG. 3 includes a perspective view of a single vial holder with the removable top included, a cross-section of the single vial holder with removable top included and a perspective view of the single vial holder with the removable top and vial cap removed.

FIG. 4 includes a perspective view with removable top included and a cross-section of the dual vial holder with removable top and vial caps removed.

FIG. 5 is a cross-section of FIG. 2 in the area of the vial holder showing the position of the vial access members relative to the septums of the vials.

FIG. 6 is a cross-section of FIG. 1 in the area of the vial holder showing the vial access member pierced through the septum of the vial.

FIG. 7 is a perspective view of the transfer apparatus shown in FIG. 1 showing the vial holder and injection device receiving areas.

FIG. 8 is a close up of FIG. 5 illustrating the vial access member piercing the septum of the vial with the collapsible vial access member shield.

FIG. 9 is a schematic of the dual vial transfer system in FIG. 2 with a first vial, a second vial, a transfer apparatus with a first and second variable pressure chambers and injection device including the fluid pathways.

FIG. 10 is a cross-section of FIG. 2 in a pre-fire position.

FIG. 11 is a schematic of the single vial transfer system in FIG. 1 with a drug vial, a transfer apparatus with a first variable pressure chamber and injection device including the fluid pathways.

FIG. 12 is a cross-section of FIG. 1.

FIG. 13 is a flow chart of a method of pressurized gas-powered transfer of medicament from a vial to an injection device in accordance with the present subject matter.

DETAILED DESCRIPTION

Figure 1:
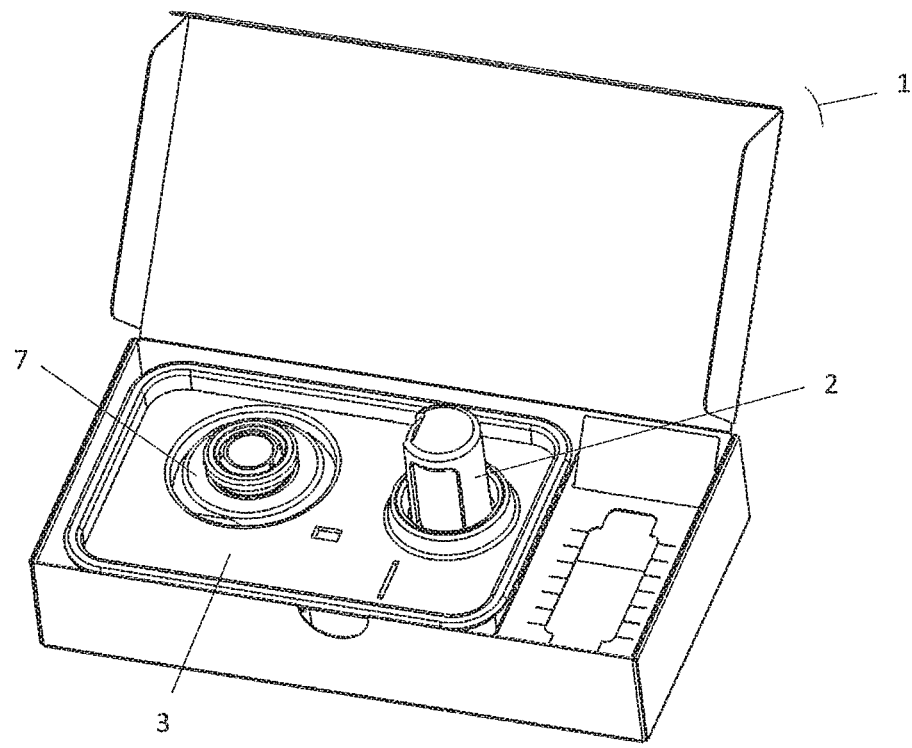
FIGS. 1-12 are exemplary views from PCT International Application No. PCT/US2014/042627, entitled Vial Transfer and Injection Apparatus and Method, which published as PCT Publication No. WO2014204894, on Dec. 24, 2014, and are included for background and general disclosure purposes.
Figure 2:
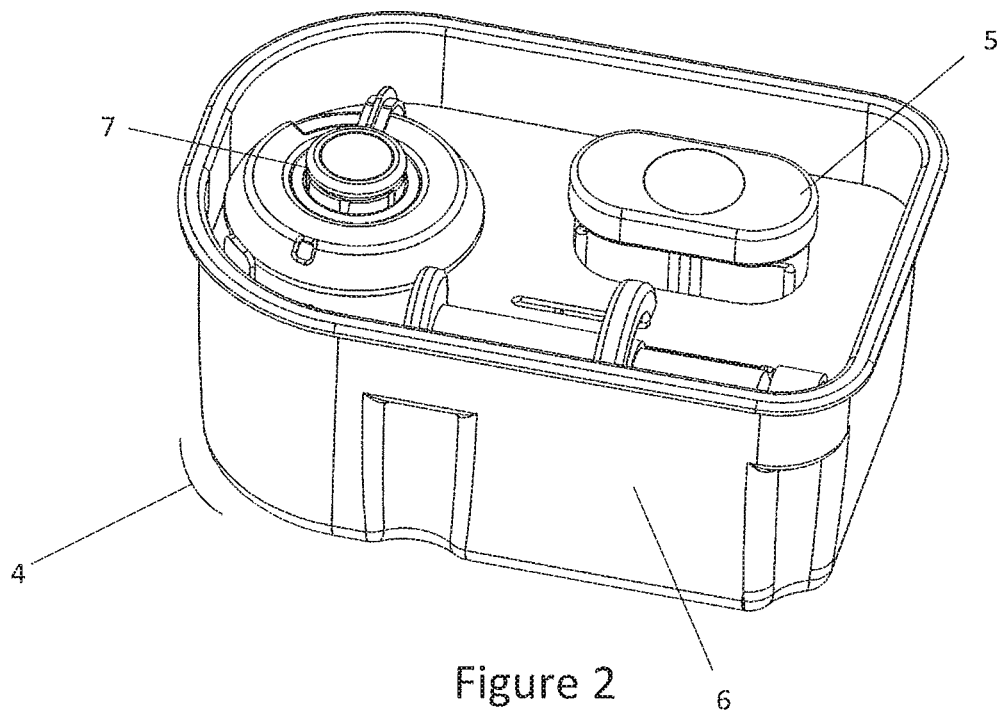

FIGS. 1-12 are provided for background and general disclosure purposes. Various functional features shown there may be employed in combination with the present subject matter. Referring to FIGS. 1 and 2, as set forth in more detail below, a disposable, one-time use, single vial transfer and injection system 1 is shown in FIG. 1 and may comprise a single vial holder 2, transfer apparatus 3 and injection device 7. A disposable, one-time use, dual vial mixing, transfer and injection system 4 is shown in FIG. 2 and may comprise a dual vial holder 5, transfer apparatus 6 and injection device 7. As mentioned earlier, each of these aspects has separate utility and may be claimed separately and/or in combination or sub-combination.

Figure 3:
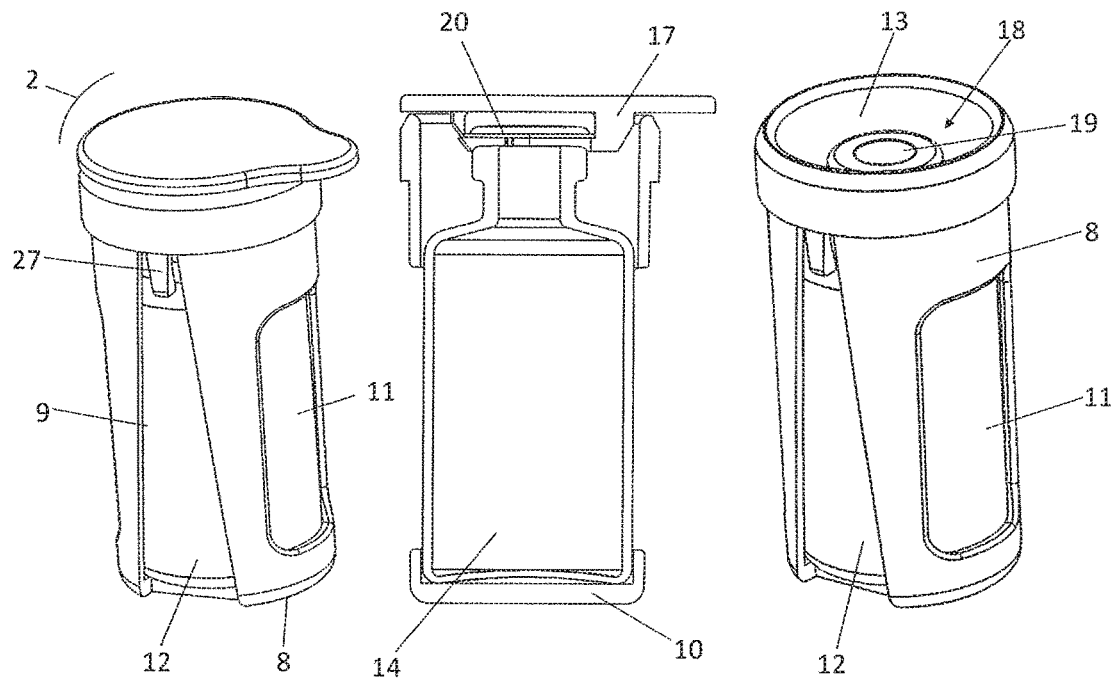
Figure 4:
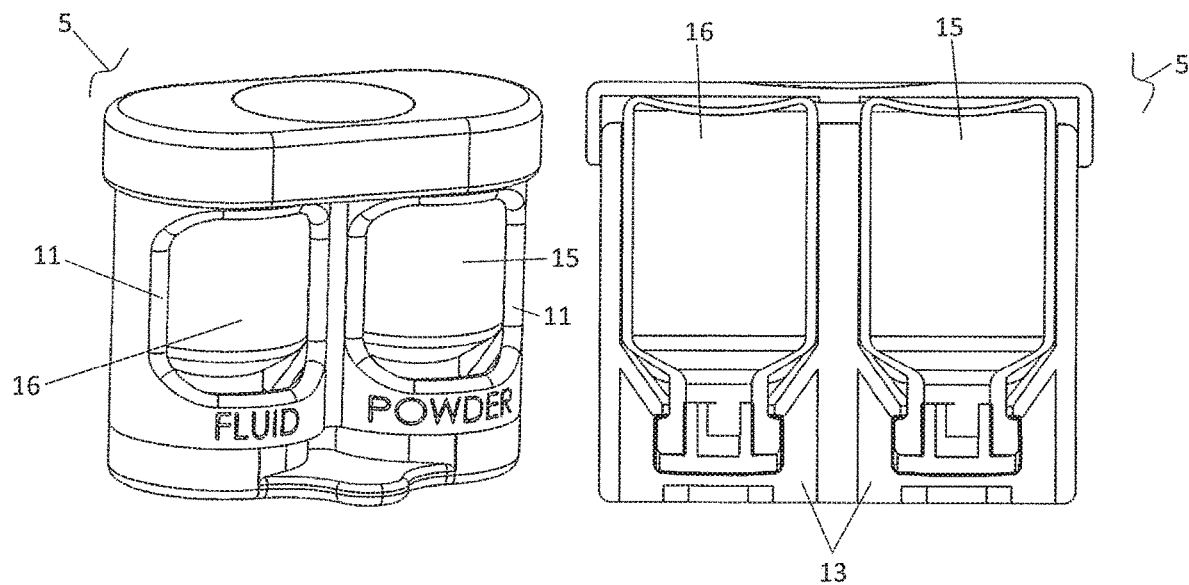

Referring to FIGS. 3 and 4, the single vial holder 2 shown includes a housing 8 that includes a side wall 9, end wall 10 and apertures or viewing windows 11. Alternatively the vial holder 2 material may be transparent to allow for visualization of the contents of the vial 12. The housing 8 is shaped to define at least one or two or more vial-receiving cavities (also referred to as stations or zones) 13 for securely holding a vial 12 in each zone 13 as shown in FIG. 4. The cavities 13 in the vial holder 5 may be sized for receiving standard injectable vial 12 of different sizes such as from 1 to 30 ml. The vial 12 may be of the same size or different sizes and may contain any desired injectable 14.

In the dual vial holder 5 illustrated in FIG. 4, the vials may include, by way of non-limiting example, one vial of powdered, lyophilized or liquid drug 15 and one vial of liquid or diluent 16. There may be variations and alternatively, for example, each vial may contain liquid medicament, or one vial contain diluent and the other vial concentrated liquid medicament. The vial holder 5 may have the vials prepackaged and assembled therein by, for example, a drug manufacturer, or the vials may be inserted into the vial holder 5 by the end user or by a medical professional such as a pharmacist or nurse. The vial holder 5 may have appropriate markings and/or features to only allow for the assembly of certain vials in certain cavities 13. For example, the powdered drug vial 15 may be inserted into a specific cavity 13 of the vial holder 5 and diluent vial 16 in another cavity 13 of the vial holder 5. The apertures or viewing windows 11 in the vial holder 5 allow for direct visualization of the contents 14 of the vials.

Referring to FIGS. 3 and 4, as a further alternative, the vial holder 5 may be an assembly of individual vial holders 2, each of which holds a single vial 12. For example, the injectable manufacturer may preassemble a vial 12 in an individual vial holder 2 which can then be joined with the vial holder 2 of another vial 12, if needed, at the time of injection. For example, a drug manufacturer may provide a lyophilized drug 15 in its own vial holder 2 and the diluent 16, such as sterile water or saline, in a separate vial holder 2. The user or medical professional can then, as needed, join the individual vial holders 2 to form the vial holder assembly 5 for connection to the transfer apparatus 6 shown in FIG. 2.

Referring back to FIG. 3, the vial holder 2 may include a removable cover 17 that normally covers and protects the end of the vial 18 during shipping and storage. Typical standard commercial vials 12 include a pierceable septum 19 located in the vial neck for accessing the vial contents 14, which is covered by a removable vial cap or closure 20. The removable cover 17 may be configured to engage the vial cap 20 so that removal of the cover simultaneously removes vial cap 20 and exposes the vial septum 19 for accessing the contents 14 after any antiseptic swabbing of the septum 19 that may be deemed necessary by the user. The vial holder 2 may recess the vial 12 therein such that after the vial cap 20 is removed by the cover 17, the pierceable septums 19 are recessed within the vial holder 2 to reduce the chance of contamination by the user prior to insertion of the vial holder 2 into the transfer apparatus 3 as shown in FIG. 1. This system is applicable to both single vial holders 2 and dual vial holders 5.

Referring to FIG. 3, the vial holder 2 may include interlocks 27 to prevent the vial 12 from being removed once the vial 12 is inserted into the vial holder 2. This helps prevent the vial 12 from falling out or being inadvertently removed during handling.

Figure 5:
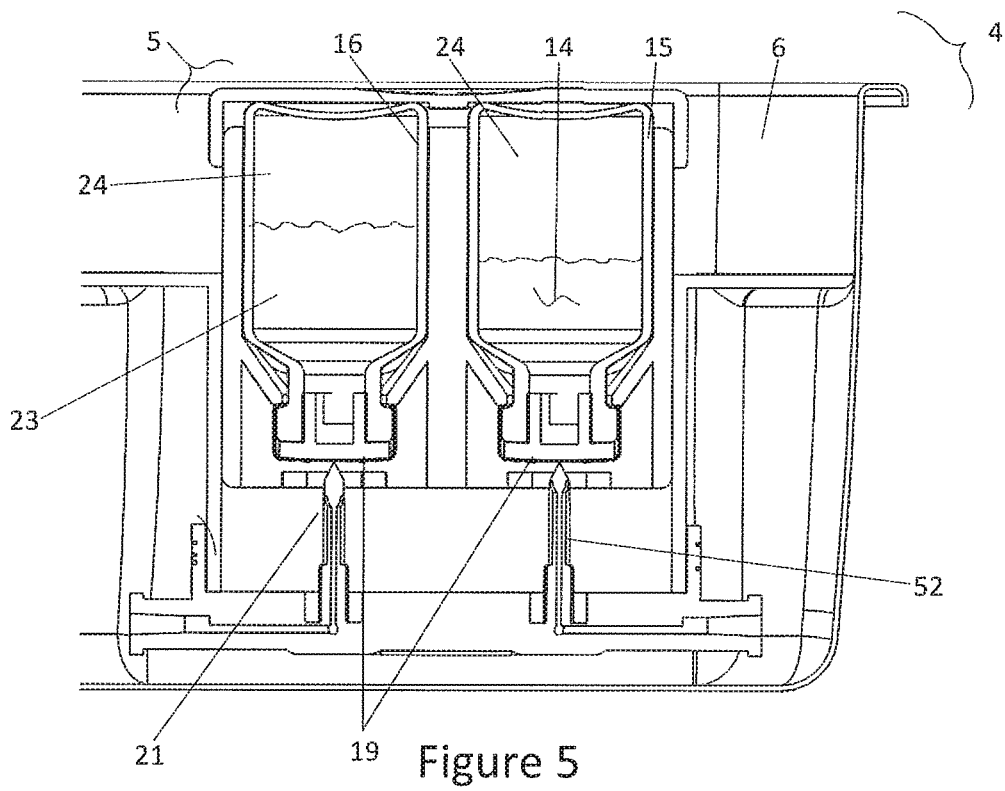

Referring to FIG. 5, the vial holder 5 may be assembled to the transfer apparatus 6 with the vial caps removed and the vials 15, 16 installed into the vial holder 5 by the device manufacturer. The exposed vial septums 19 are held in close proximity to the vial access members 21, 52 prior to activation. This configuration provides convenience by eliminating the need for the user to remove the vial caps, swab the vial tops 19 and assemble the vial holder 5 to the transfer apparatus 6 prior to use of the system 4.

Figure 6:
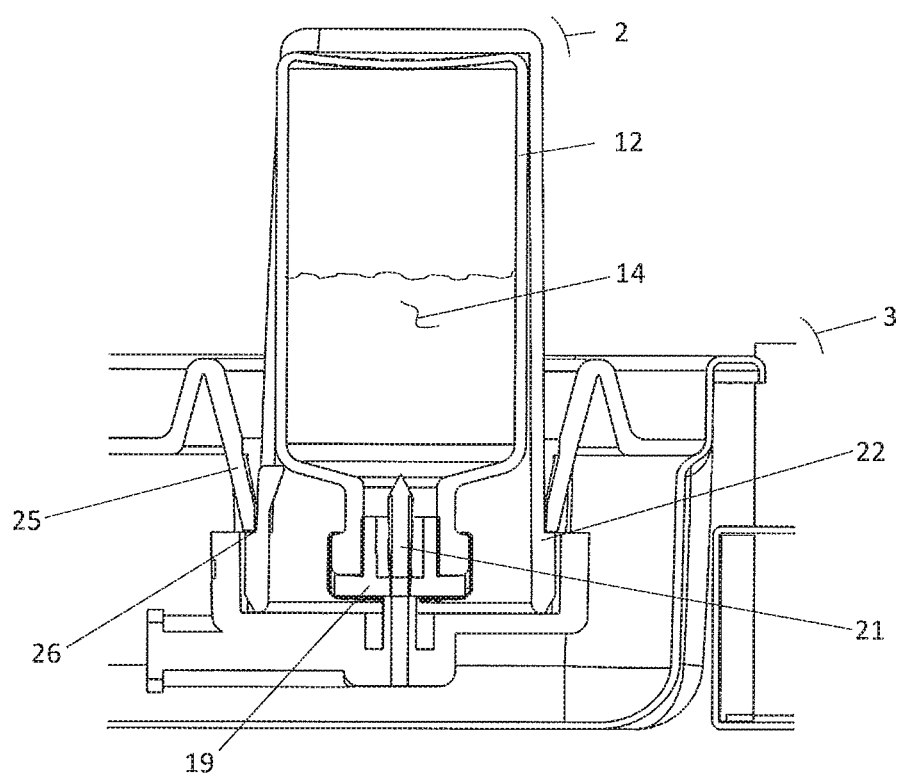

Referring to FIG. 6, the vial holder 2 may be packaged separately from the transfer apparatus 3. In this case, the user would remove the vial cap with the removable cover 17, swab the vial top 19 (if necessary) and assemble the vial holder 2 into the transfer apparatus 3. As shown in FIG. 6, the vial holder 2 may include lock-out features 22 that interact with the transfer apparatus 3 to prevent the vial holder 2 from being inadvertently pulled out of the transfer apparatus 3 after activation by the user.

Referring to FIG. 5, the vial holder 5 preferably is assembled to the transfer apparatus 6 to configure the vials 15, 16 upside down in a vertical position. This allows any liquid 23 in the vials to be in direct communication with the vial access members 21, 52 after insertion of the vial holder 5. This also forces the air 24 to the top of the vial in this orientation. To encourage the septums 19 to remain uncontaminated after removal of the vial caps and before insertion of the vial holder 5, the exposed vial septums 19 may be recessed into the vial holder 5 to prevent inadvertent contact as shown in FIG. 4. This configuration is applicable to single vial holder and dual vial holder configurations.

Referring to FIG. 6, the vial holder 2 preferably is mechanically configured with insertion features 25 in the transfer apparatus 3 to actuate like an on/off switch, i.e., to only have two states, open and closed such as a light switch. This may prevent the user from pushing the vial holder 2 into the transfer apparatus 3 half way and not allowing the vial access member 21 to pierce the septum 19 and allow communication between the contents 14 of the vial 12 and the transfer apparatus 3. Additionally, the vial holder 2 may interface with an interlock 26 in the transfer apparatus 3 to lock the vial holder 2 in the closed position after full insertion of the vial holder 2 to prevent the vial holder 2 from being removed from the transfer apparatus 3 after insertion.

Figure 7:
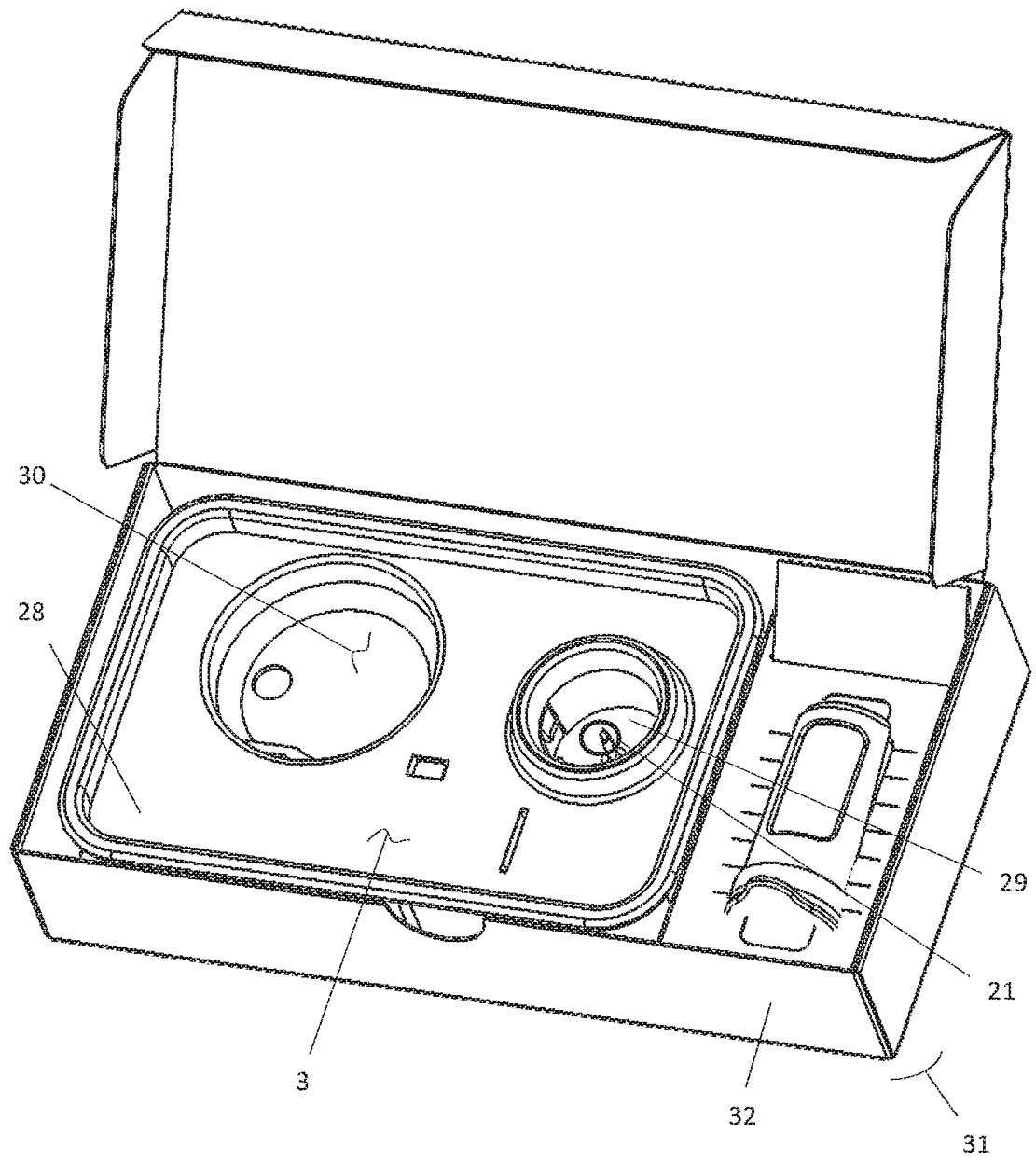

Referring to FIG. 7, the transfer apparatus 3 comprises an outer housing 28 and defines a vial holder docking area or first receiving station 29 and an injection device docking station or second receiving station 30 (for removable injection devices). In the illustrated structure, the vial holder docking station 29 and injection device docking station 30 are at opposite ends of the transfer apparatus housing 28.

Referring to FIG. 7, the transfer apparatus 3 may have an outer housing 28 that is integrated into the packaging 31 of the system. The outer packaging 31 may essentially form the bottom and side walls of the transfer apparatus outer housing 28. All of the operational steps in using the system up to the point of removal of the injection device may occur in this packaging 31. This may provide cost reduction and increase ease of use for the user. Additionally, incorporating the entire transfer apparatus 3 into the packaging 31 eliminates the possible user error that could occur if the user was required to remove the transfer apparatus 3 from the package 31. The packaging 31 could include a plastic tub or tray that contains the system. Furthermore, the packaging 31 could include everything within a shipping carton 32 that houses the entire system.

Figure 8:
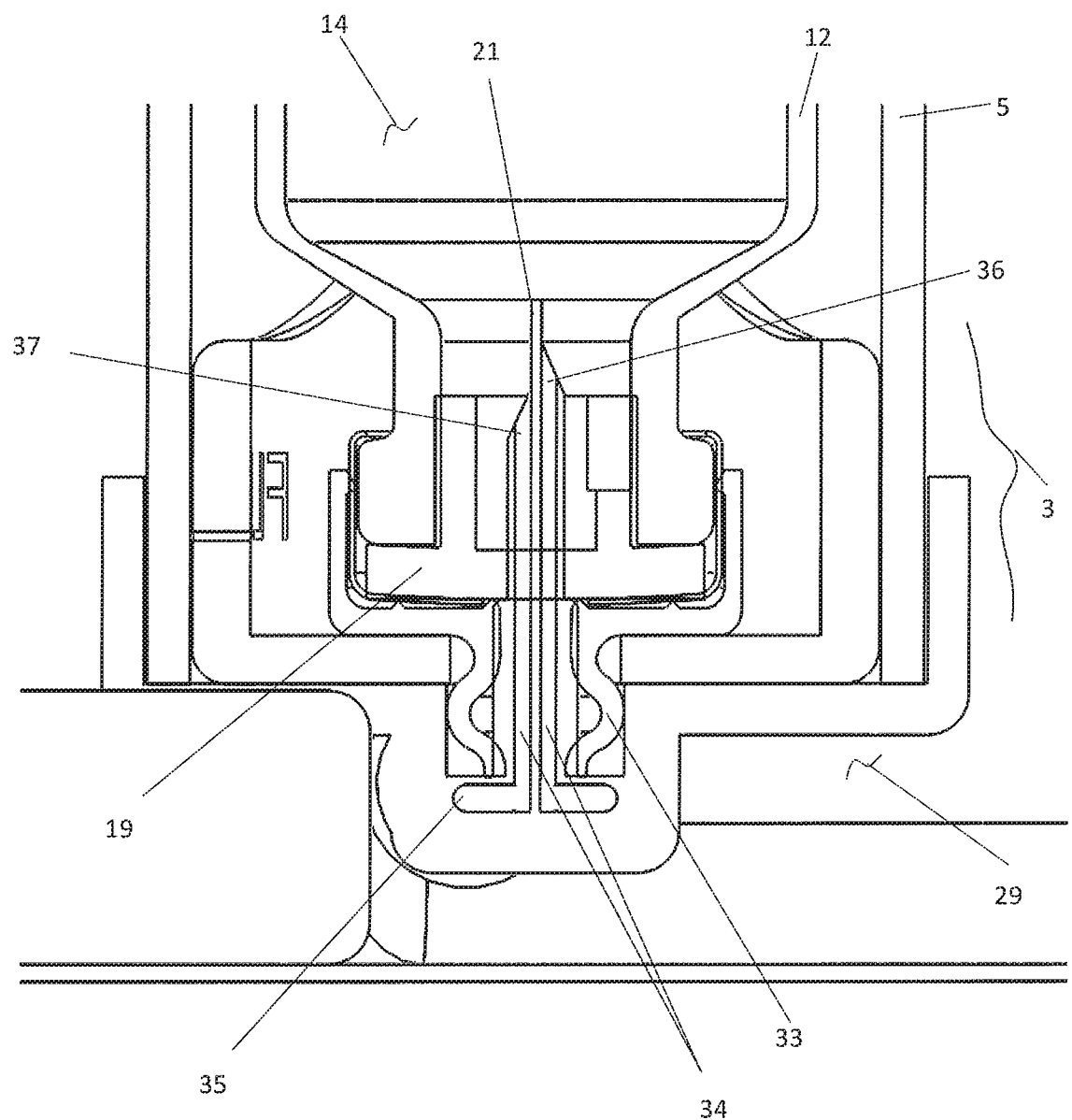

Referring to FIG. 7, the transfer apparatus 3 comprises a vial holder docking area 29 that may include elongated a vial access member or piercing member 21. This access member or piercing member 21 could be configured as pointed or blunt cannulas or needles. Referring to FIG. 8, the vial holder 5 with attached vial 12 is shown inserted into the vial docking station 29 and the vial access member 21 piercing the vial septum 19 allowing access to the contents 14 of the vial 12. The vial access member 21 may include a collapsible seal 33 to maintain sterility of the vial access member 21 and fluid path prior to activation. The collapsible seal 33 may also attach and seal on the outside of the vial 12 relative to the vial access member 21 to maintain sterility prior to activation.

Referring to FIG. 8, the vial access member 21 of the transfer apparatus 3 may comprise of multi-lumen tubes 34 to communicate with the internal fluid pathways 35 of the transfer apparatus 3. The vial access member 21 preferably comprises one inlet tube 36 allowing air or fluid to enter the vial 12 and one outlet tube 37 allowing for air or fluid to exit the vial 12. These inlet 36 and outlet 37 tubes may be separate and distinct and communicate with different fluid pathways in the transfer apparatus 3. Because of the vertical orientation of the vial 12 in the upside-down position, the lumen openings 38 in the vial access member 21 can be oriented so the inlet tube opening 36 is above the output tube opening 37. This orientation allows for introduction of pressurized air or liquid through the upper inlet tube 36 and output of the vial contents 14 through the lower output tube 37. Further, the outlet opening 37 may be positioned near the bottom of the vial 12, adjacent to the septum 19 to encourage the entire contents 14 of the vial 12 to enter the outlet port 37 and be removed from the vial 12.

Figure 9:
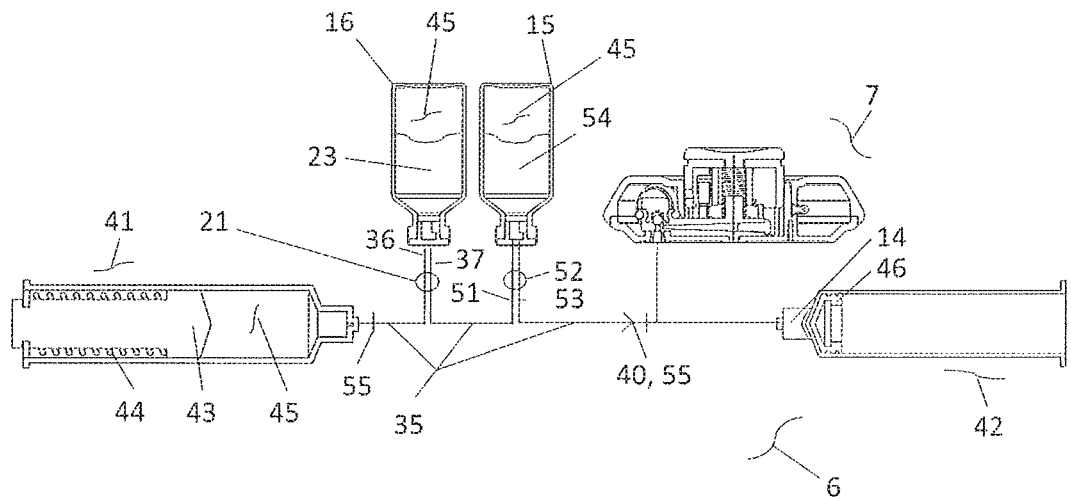
Figure 10:
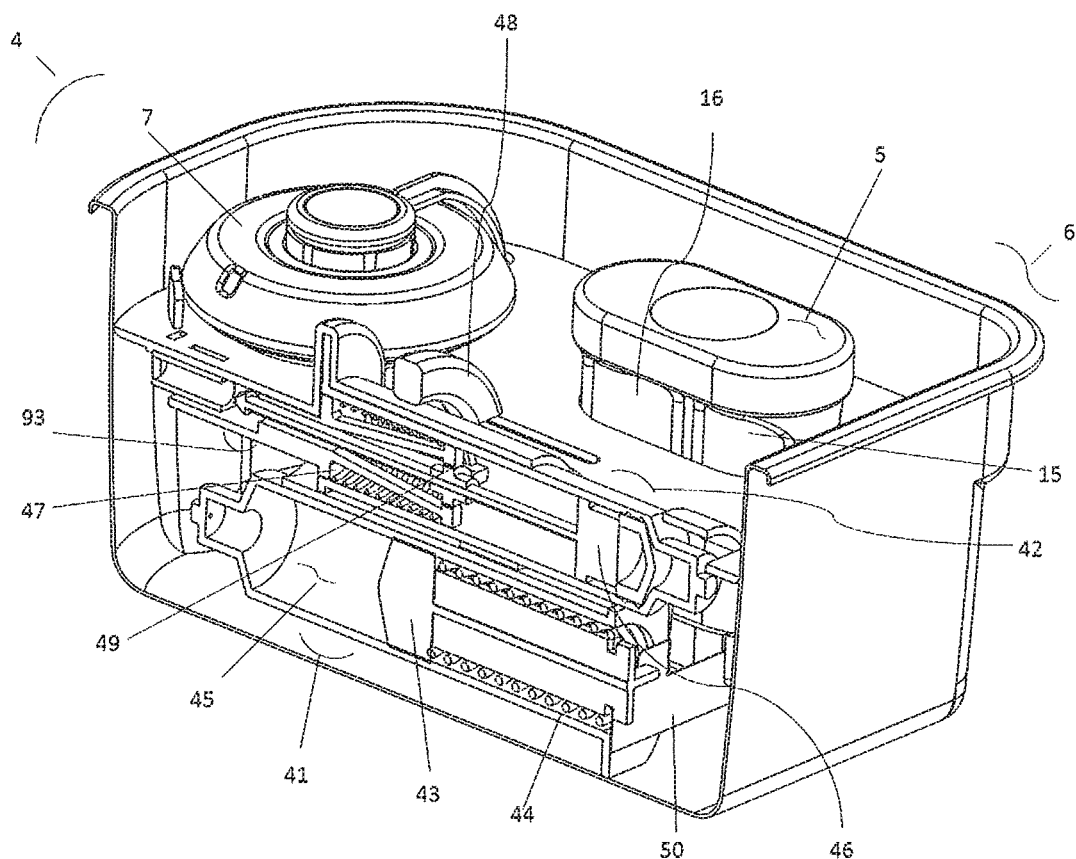

Referring to FIGS. 9 and 10, the transfer apparatus 6 is configured to carry out all of the necessary steps to transfer, mix and/or reconstitute (if necessary) injectable 14 contained within the vials 15,16 and transfer the mixture to the injection device 7 preferably automatically after user initiation of the process. The transfer apparatus 6 is configured and preferably includes a propulsion system or systems, such as electrically (e.g., battery powered) or mechanically (e.g., spring loaded) actuated pumps, to direct diluent from the diluent vial 16 into the injectable powder vial 15 and to direct the injectable 14 through the transfer apparatus 6 into the injection device 7.

Referring to FIGS. 9 and 10, the transfer apparatus 6 may also include an array of internal fluid pathways 35, as required to perform any transfer, reconstitution, mixing, dilution or other processing of the injectable 14 and transferring it from the vials 15, 16 in the vial holder 5 to the injection device 7. The fluid pathways 35 may include flexible or rigid conduits or tubes. These fluid pathways 35 may also include check valves, filters, flow restrictors or other means 40 to direct the drug from the vials 15, 16 through transfer apparatus 6, into the injection device 7.

Referring to FIGS. 9 and 10, the transfer apparatus 6 may include variable volume pressure chambers or cylinders that have movable spring-loaded pistons therein and directly communicate with the internal fluid pathways 35.

These chambers would not be required in the embodiment described in the Summary and in more detail below, which employs a pressurized gas source to poser the fluid transfer and/or mixing. In the embodiment of FIGS. 9 and 10, the chamber capacity for each variable volume chamber may be defined by chamber diameter and location of the piston within the chamber. The first pressure chamber 41 in transfer apparatus 6 may preferably have an initial volume set by the manufacturer in the range of 1 to 30 milliliters. The initial contents of the first pressure chamber 41 may preferably include air 45. The piston 43 may be driven by a compression spring 44 in the first pressure chamber 41 whose volume is defined and set by the manufacturer. The spring-loaded piston 43 may be of adequate size and configuration to produce 1 to 50 psi of static air pressure in the first pressure chamber 41. The volume of air 45 will depend on the diameter of the chamber 41 and stroke position of the piston 43 during operation. This pressure will depend on the relative volume of air 45 displaced by the piston 43 and the force exerted by the spring 44. In other words, the force exerted by the spring 44 multiplied by the area of the piston 43 inside the chamber 41 will determine the static pressure within the chamber 41. The force exerted by the spring 44 at its solid height or the beginning of the stroke may be much higher than the force exerted by the spring 44 at end of its travel. The spring 44 may be appropriately sized to control the rate at which air 45 is expelled out of the pressure chamber 41 and thus the speed of the fluid transfer in the transfer apparatus 6. The first pressure chamber 41 is preferably configured to expel all of the air 45 out of the first pressure chamber 41. Alternatively, a flow restrictor 55 in the output path 35 of the pressure chamber 41 could be used to control the rate at which air 45 is expelled out of the pressure chamber 41.

Referring to FIGS. 9 and 10, the chamber volume for the second pressure chamber 42 may be set by the manufacturer. Alternatively, the filled chamber volume for the second pressure chamber 42 may be set by the user at time of use using a dose selector or volume controller 48 in the range of 0.5 to 30 milliliters. The spring-loaded piston 46 in the second pressure chamber 42 may be of adequate size and configuration to produce 1 to 200 psi of pressure in the second pressure chamber 42. A dose selector or volume controller 48 permits the user to select a prescribed dosage to be injected by the injection device 7 by setting the filled volume of chamber 42. The dose selector 48 may be of any suitable configuration. The dose selector 48 may be directly coupled to the pressure plunger assembly chamber 93 which is moveable inside the pressure chamber 42. A trigger 49 within the pressure plunger assembly 93 releases the piston 46 in the second pressure chamber 42 once the piston has reached a position corresponding to the filled volume setting. The user selects the desired dosage positions in the second pressure chamber 42 by moving the dose selector 48 which positions the pressure chamber plunger assembly 93 to define a filled chamber volume equal to the desired injection dosage. Alternatively, the position of the pressure plunger assembly 93 may already be set by the manufacture corresponding to the delivery dose and the user operates the device without making a dose adjustment.

Referring to FIGS. 9 and 10, the transfer apparatus 6 for a dual vial system 4 that provides for mixing and transfer includes a vial holder 5 with a first vial 16 and second vial 15, a first variable volume pressure chamber 41, a second variable volume dose pressure chamber 42, fluid pathways 35, and check valves 40 to direct air from the first pressure chamber 41 into the first vial 16 and the contents 23 of the first vial 16 into the second vial 15 and the resulting mixture 14 in the second vial 15 into the second pressure chamber 42 which is then transferred into the injection device 7.

Referring to FIG. 8, upon complete insertion of the vial holder 5 into the transfer apparatus 6 and the subsequent introduction of the vial access members 21 through the septums 19 and into the vial chambers 12 by the user allows for the release of the pressure chamber trigger 50 shown in FIG. 10.

Referring to FIGS. 9 and 10, release of the trigger 50 then releases the first pressure chamber spring 44 allowing the advance of the first pressure chamber piston 43 in the first pressure chamber 41 causing the air 45 in the first pressure chamber 41 to be forced through the inlet tube 36 of the first vial access member 21 and into the first vial 16 through internal passage ways 35 in the transfer apparatus 6. As more air 45 is forced out of the first pressure chamber 41 and into the first vial 16 through the inlet tube 36, the air 45 rises to the top of the first vial 16 due to its vertical orientation within the vial holder 5. The increasing air pressure in the first vial 16 causes the fluid 23 in the vial 16 to be expelled through the outlet tube 37 of the first vial access member 21 and through the inlet tube 51 of the second vial access member 52. The fluid 23 from the first vial 16 entering the second vial 15 mixes with the contents 54 of the second vial 15 containing the liquid or powdered medicament and exits though the outlet tube 53 of the second vial access member 52 and into the second pressure chamber 42. In the same manner within the reconstitution configuration, the advancing plunger 43 in the first pressure chamber 41 continues to push a first fluid 23 then air 45 mixture through the first vial 16 into the second vial 15. The increasing air pressure in the top of the second vial 15 causes the reconstituted or other mixture 14 in the bottom of the second vial 15 to be expelled out into the second pressure chamber 42. A 'popoff' or check valve 40 or other type of valve may be present on the outlet tube 53 of the second vial access member 52 to encourage all of the contents 23 of the first vial 16 to enter the second vial 15 before the contents 14 of the second vial 15 are expelled out into the second pressure chamber 42. The valve would not open until the pressure corresponding to the plunger 43 pushing substantially all the air 45 out of the first pressure chamber 41. This ensures that the contents 54 of the second vial 15 may be thoroughly mixed with the contents 23 of the first vial 16 before the mixture 14 exits the second vial 15 and into the second pressure chamber 42. Alternatively, a flow restrictor 55 may be used in the fluid pathway 35 to delay the transfer and increase the mixing time.

Referring to FIGS. 9 and 10, injectable drug 14 flows from the second vial 15 after mixing, diluting and/or reconstitution, into the second pressure chamber 42, filling the chamber 42 to the extent permitted by the piston 46 position as selected using the dose indicator 48 by the user or manufacturer, which corresponds to the desired dosage. When the desired volume of the second pressure chamber 42 has been achieved, the second pressure chamber trigger 49 releases the spring 47 and forces the piston 46 forward, expelling the selected dosage of injectable drug 14 under pressure into the injection device 7. Calibration of the dose volume shown on the dose selector 48 and the actual dose received by the user may be required to account for fluid loss in the internal pathways 35 of the transfer apparatus 6. The injection device 7 is now full and ready to remove from the transfer apparatus 6.

Figure 11:
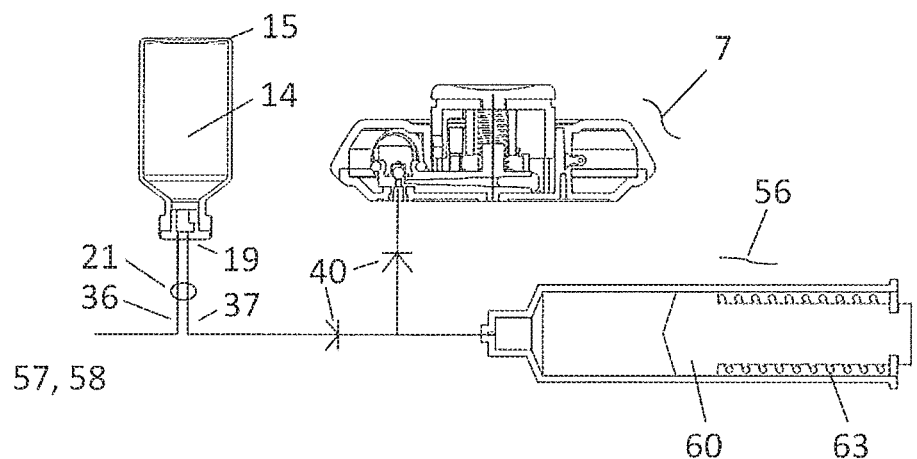
Figure 12:
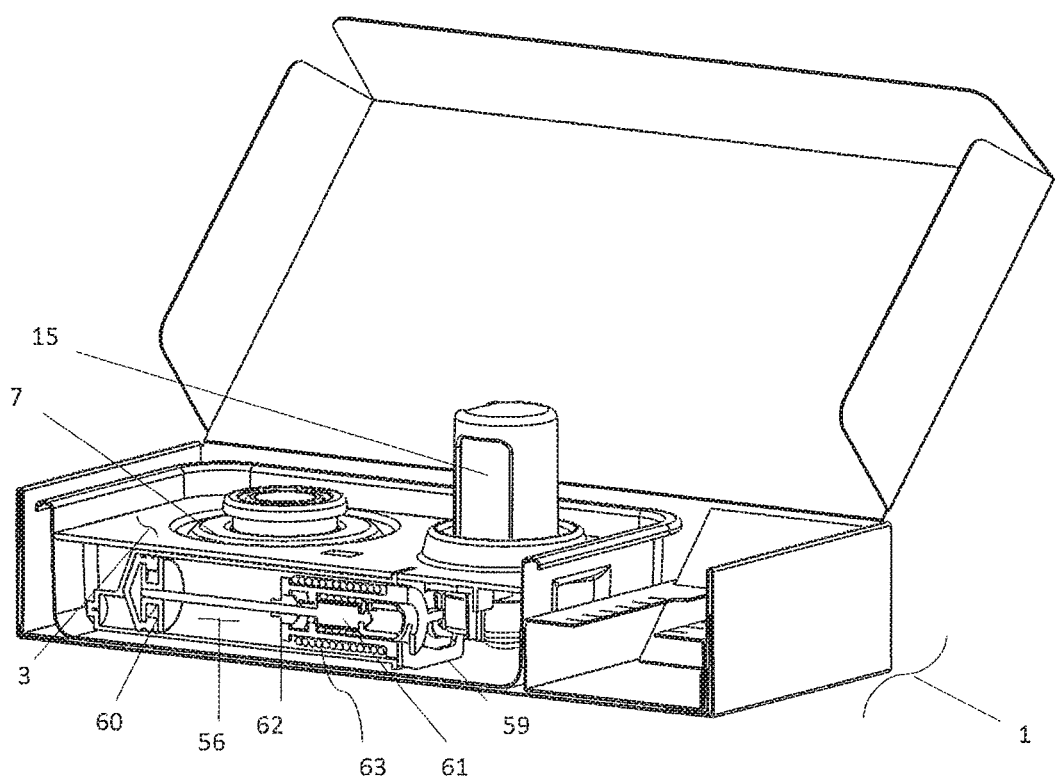

Referring to FIGS. 11 and 12, an alternative transfer apparatus 3 within a single vial system 1 that does not perform mixing but only transfers fluid 14 from a single vial 15 to the injection device 7 is provided. This alternative transfer apparatus 3 includes a vial holder 2 with single vial 15, a variable volume pressure chamber 56, fluid pathways 35, and check valves 40 to direct the contents 14 from the vial 15 into the injection device 7. The inlet tube 36 of the vial access member 21 is vented to the environment 57 to allow air 58 to enter the vial 1. The outlet tube 37 of the vial access member 21 is connected to the pressure chamber 56.

Referring to FIGS. 11 and 12, the full insertion of the vial holder 2 into the transfer apparatus 3 by the user causes the introduction of the vial access member 21 through the septum 19 of the vial 15 to access the contents 14 of the vial 15. This also triggers the release of the pressure chamber trigger 59. The pressure release trigger 59 releases the plunger 60 within the pressure chamber 56 connected to a withdraw spring 61. The withdraw spring 61 forces the plunger 60 to retract and withdraw fluid 14 from the vial 15 and fill the pressure chamber 56. A specified amount of fluid 14 withdrawn by the chamber 56 could be set by the manufacturer by limiting the retraction of the plunger 60. Additionally, the chamber 56 can be configured to withdraw all of the fluid 14 from the vial 15 by retracting the plunger 60 to its full travel. Once the plunger 60 reaches a set position within the pressure chamber 56, it interacts with a dispense trigger 62 that releases a dispense spring 63 to force the liquid 14 out of the pressure chamber 56 into the injection device 7. Check valves 40 could be employed to prevent fluid 14 from going back into the vial 15.

Pressurized Gas-Powered Transfer and/or Mixing

In accordance with the present subject matter shown in FIGS. 13-24, the transfer and/or mixing and re-suspension are powered by a pressurized air source, such as a pressure vessel, which may be in the form of pre-filled pressure cylinder or cartridge. This allows for the elimination of the variable volume pressure chambers or cylinders that have movable spring-loaded pistons as described above and provides potential reduction in cost and size for the transfer and mixing/re-suspending apparatus.

Turning now to FIG. 13, this flow chart provides an overview of a single vial fluid transfer method and generally depicts some exemplary steps in using a pressurized gas source to power the transfer. The structures and more specific aspects of the structures for carrying out the process or method will be described later.

Every step in FIG. 13 may not be required in all embodiments. As reflected in the flow chart, a vial containing liquid medicament is inserted into a vial receiving station of the transfer device, which may have a spike for piercing the vial septum and accessing the contents. The spike may have two lumen, one for entering gas and another for outflow of medicament, or two separate spikes may be used.

The method is initiated by the user by actuating a gas triggering mechanism which may be of various different configurations. As explained later, the triggering mechanism may be actuated upon insertion of the vial into the vial receiving station or thereafter. For example, the insertion may release a spring force that forces a piercing or puncturing pin through a sealing diaphragm or cap associated with a pre-filled pressure cylinder or cartridge. Alternatively, the user's own force when inserting the vial into the receiving station may be employed to force together a pre-filled gas cylinder and piercing pin to access the pressurized gas. These are only a couple of non-limiting examples.

The pre-filled pressurized gas cartridge or cylinder may contain gas under very high pressures, such as 500 psig or more, for example 900 psig or greater, and even up to 2,000-3,000 psig or more. Accordingly, it may be desired to direct the pressurized gas flowing from the pressure cylinder or cartridge through a flow restrictor, such as a small orifice, and/or a pressure regulator to control the gas flow rate and/or gas pressure before it enters the vial.

The pressurized gas is directed into the vial, and the pressure of the gas forces liquid medicament from the vial and into an injection device. A feedback mechanism may be provided to indicate when the contents of the vial have been fully transferred to the injection device, and a vent may exhaust surplus gas to the ambient atmosphere. Because the volume of the pre-filled cylinder is small, such as 5 ml or less, or even 2 ml or less, the gas vented into the atmosphere will be relatively de minimus and may not even be noticeable to the user.

After transfer to the injection device is completed, the injection device may be removed from the transfer device and used in the manner previously described in the earlier identified PCT publication WO2014/204894.

Figure 14:
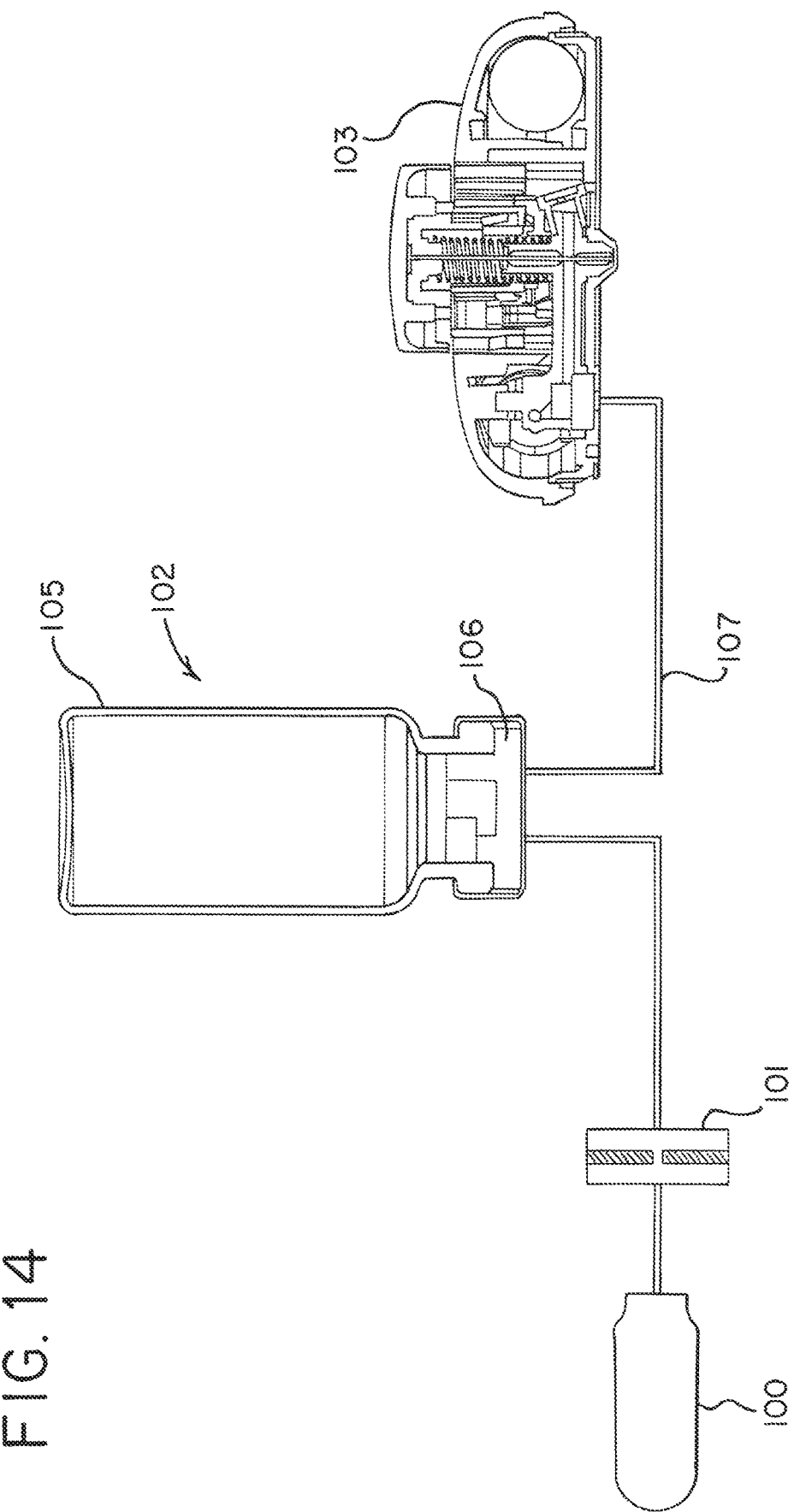
FIG. 14 is a flow diagram of a method of pressurized gas transfer of medicament from a vial to an injection device in accordance with the present subject matter.

FIG. 14 is a diagrammatic view of the single vial transfer system, including a pressure vessel in the form of a prefilled pressurized gas cylinder or cartridge 100, a flow restrictor and/or pressure regulator 101, a liquid medicament vial 102 and an injection device 103. The gas cylinder may be any suitable cylinder commercially available or may be a custom cylinder. For example, a variety of potential cylinders are available from Leland Gas Technologies of South Plainfield, N.J., USA, which manufactures high pressure gas filled disposable cylinders in capacities from 1 to 1000 cc. The cylinders may be charged to suitable pressures up to 2000-3000 psig or more. It is understand that relatively small capacity disposable cylinders will be suitable for the present subject matter. For example, the cylinder may have a volume of 10 ml or less, and more preferably less than 5 ml, such as 1-2 ml, pressurized to 500 psig or more, such as from 900 psig up to 2000-3000 psig or more.

The gas may be any suitable gas, such as, but not exclusively, an inert gas. As it will come in contact with medicament, the gas is preferably pathogen free—i.e., free of active pathogens. Nitrogen or argon may be suitable gases. When released from the cylinder, such as by puncture by a piercing pin, the gas is directed through a suitable flowpath from the cylinder through the flow restrictor and/or pressure regulator 101 to the vial 102.

The flow restrictor and/or pressure regulator 101 may be of any suitable configuration, preferably small and disposable. A typical flow restrictor may be a diaphragm with a small orifice to limit the flow rate of gas from the cylinder. If desired a pressure regulator may also be included in combination with or separate from the restrictor. From the restrictor/regulator, flow path 104 conducts the gas to the vial 102.

The vial 102 may be a standard drug vial with a rigid container portion 105 usually glass, open at one end and sealed by a piercable diaphragm or septum 106 of latex, silicone or other material. The present process is preferably carried out with the vial in inverted vertical position so that the gas flows to the closed end of the vial, forcing essentially all the medicament from the vial under the force of the pressurized gas.

From the vial, flow path 107 directs the medicament under the pressure of the gas to a suitable vessel such as an injection device 103. The injection device has a medicament reservoir, such as an expandable reservoir for receiving the medicament, for example a reservoir that expands under pressure from the medicament. The reservoir may be biased to expel the medicament upon user actuation of the injection device. In the illustrated embodiment, the injection device 103 has an elastomeric expandable bladder that is initially empty and expands as it is filled with medicament flowed thereinto under the force or pressure of the gas from cylinder 100. The elastomeric quality of the bladder biases it to expel the medicament into the subject when later activated by the user, as described in the previously filed PCT application identified above.

Figure 15:
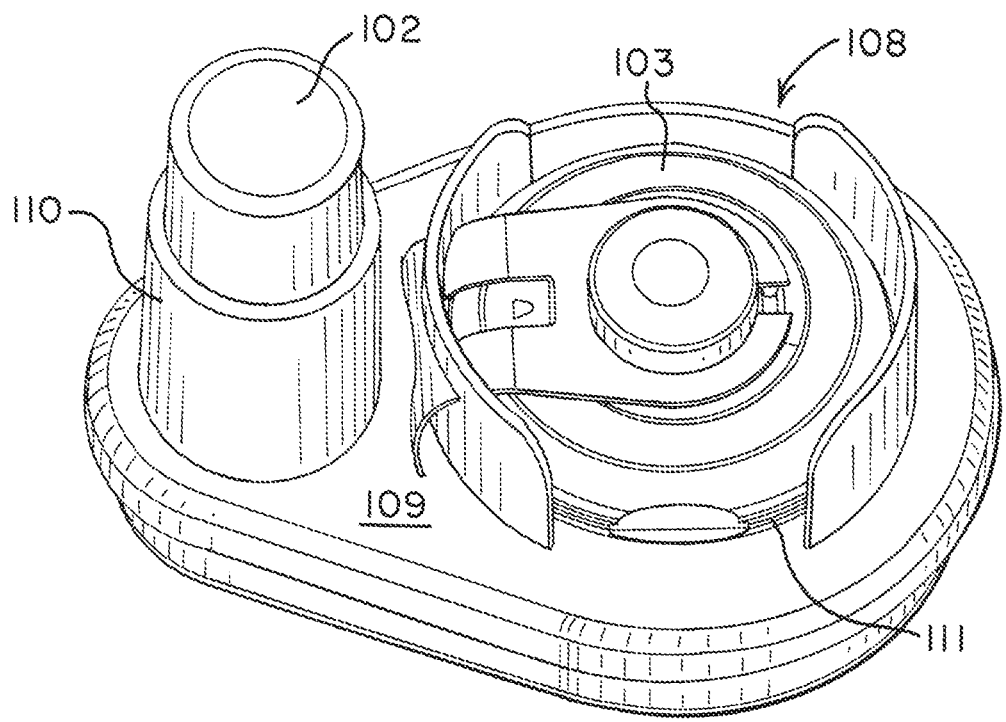
FIG. 15 is a perspective view of a single vial transfer device embodying one aspect of the present subject matter.

FIG. 15 illustrates one potential transfer device, generally at 108, for effecting the transfer of liquid medicament from a vial 102 to an injection device 103 as generally described above. The illustrated transfer device has a rigid plastic housing 109 that includes a vial receiving station 110, shown with vial 102 inserted, and an injection device receiving station 111, shown with the injection device 103 in place. The housing 109 contains the fluid flow paths and various operative mechanisms for effecting the transfer of medicament to the injection device from the vial.

Figure 16:
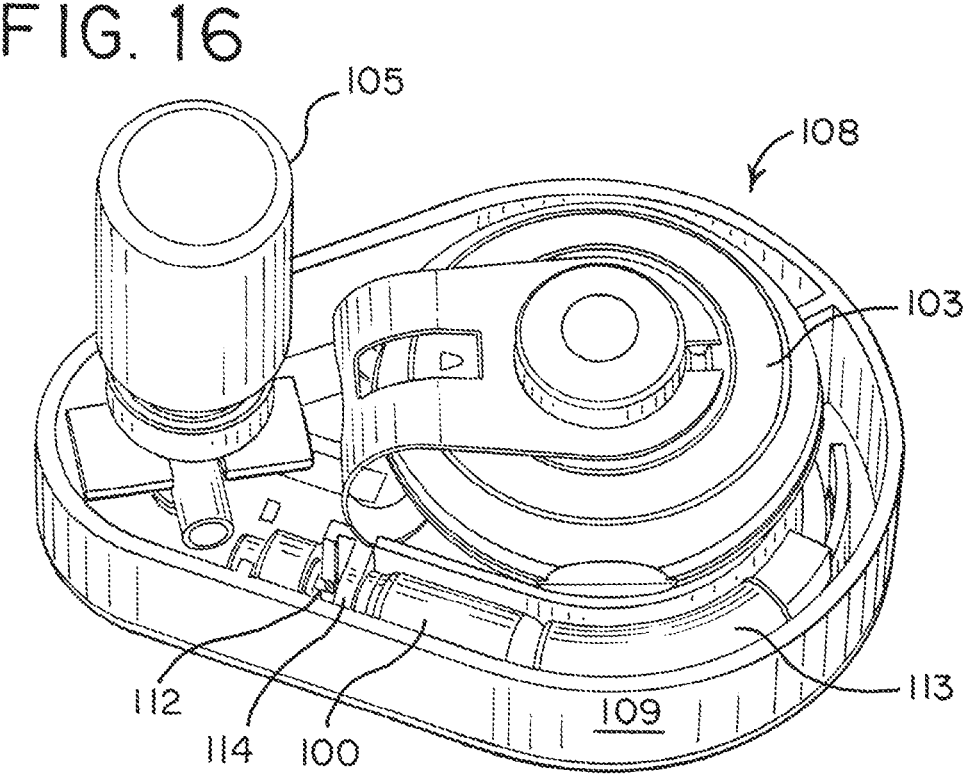
FIG. 16 is a perspective view of the device of FIG. 15, with a housing portion removed for better view of the interior.

This may be better seen in FIG. 16, which is similar to FIG. 15 but with the upper part of the housing 109 removed to allow viewing of certain of the inner parts. The fluid flow paths, which may be of any suitable configuration, such as plastic tubing, are not visible in FIG. 16. With the removal of the upper part of the housing in FIG. 16, the gas cylinder or cartridge 100 may be seen in the pre-fill or pre-fire position, before the gas is released by a piercing pin 112. In the pre-fill position, the cylinder is positioned between a compressed spring, generally shown as member 113, and a pivotable or slidable latch or lever 114 that blocks movement of the gas cylinder toward the piercing pin. Insertion of the vial 102 into the vial receiving station simultaneously forces one or more access spikes (not seen in FIG. 16) through the vial septum 106 and depresses latch 114. When latch 114 is depressed, it releases the pressurized gas cylinder 100 for movement against the piercing pin 112 under the force of compressed coil spring 113. This causes the pin to pierce a puncture area or sealing cap on the pressure cylinder and allows the compressed gas to flow from the cylinder through the pin. Although described with the spring 113 forcing the cylinder 100 against the pin 112, alternatively the pin could be moved against the cylinder. Also, other types of force-generating devices other than a coil spring could be utilized.

Figure 17:
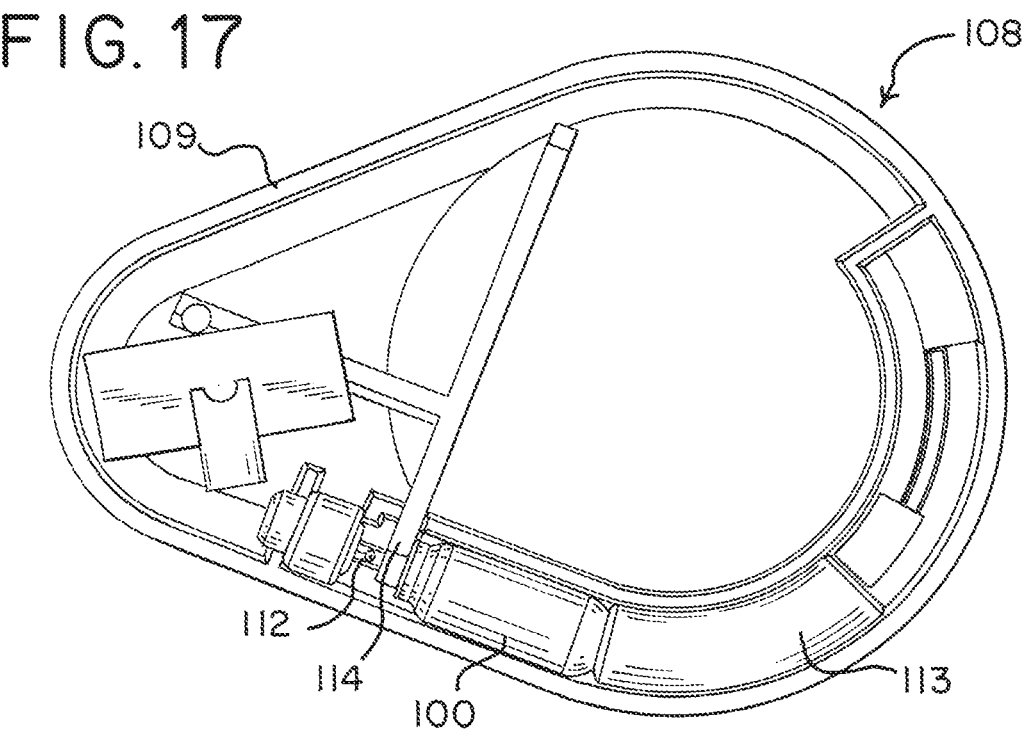
FIG. 17 is a horizontal cross-sectional view of the device of FIG. 15.

FIG. 17 is a top view of the lower portion of housing 109, with the vial 102 and injection device 103 removed to better illustrate the respective positions of the pressure cylinder 100, compressed spring 113 and latch 114. The position shown is with the latch blocking movement of the cylinder and prior to puncture of the pressurized gas cylinder by the piercing pin 112.

Figure 18:
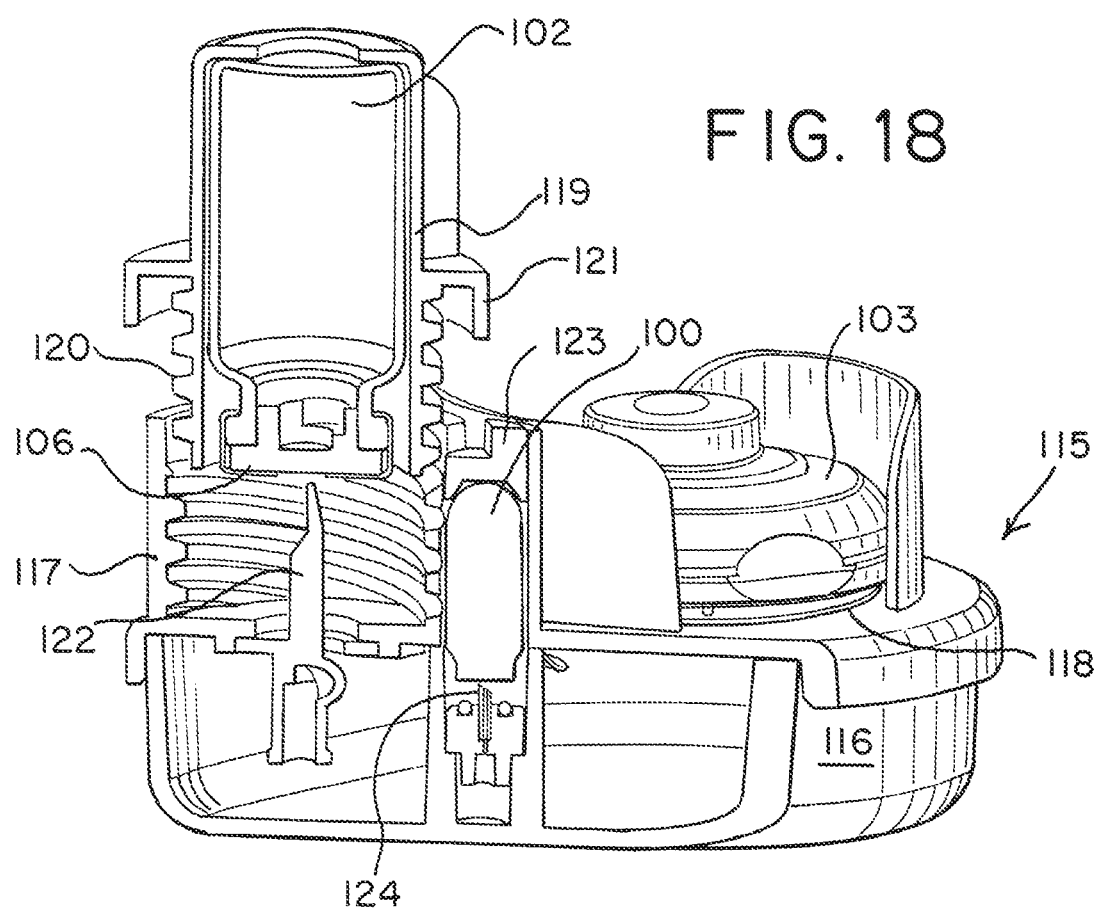
FIG. 18 is a perspective view, partially in section, of an alternative single vial transfer device embodying an aspect of the present subject matter.
Figure 19:
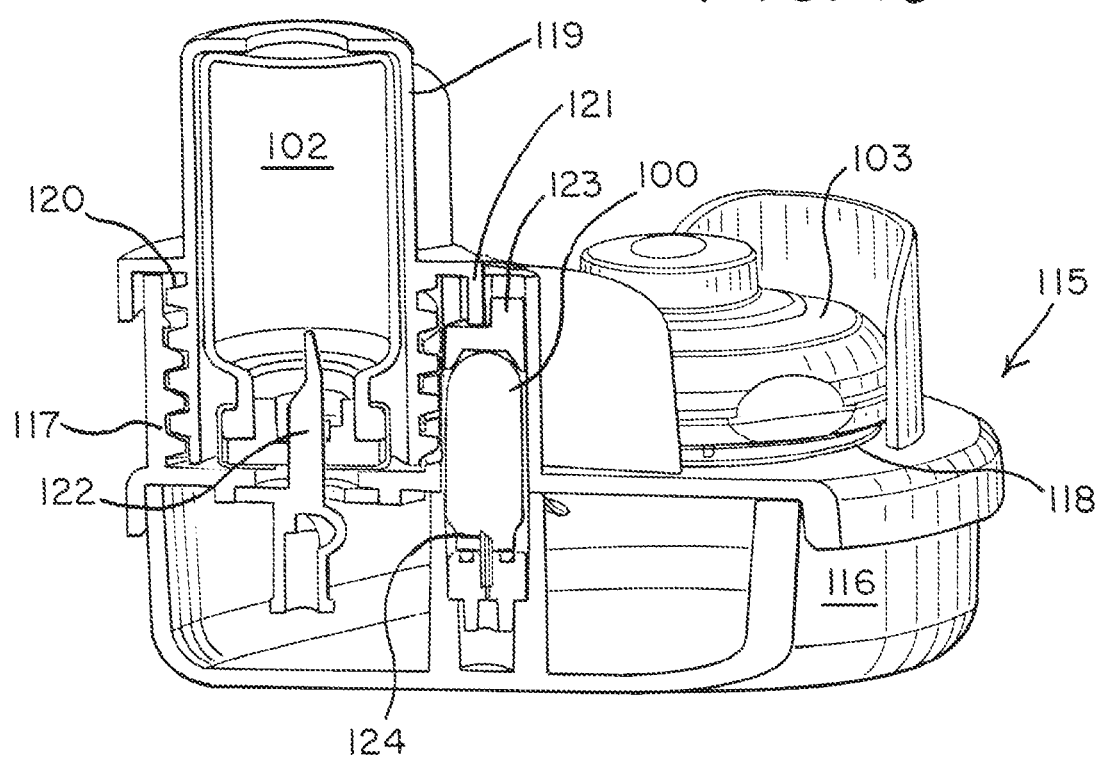
FIG. 19 is a perspective view, partially in section, of the device of FIG. 18 in a different operative position.

FIG. 18 shows one possible alternative transfer device with a different arrangement for insertion of the vial 102 to cause puncture of the pressure cylinder 100. The transfer device 115 includes a housing 116 with a vial receiving station 117 and an injection device receiving station 118 with the vial 102 and injection device 103 shown in their respective stations. In this embodiment, the vial 102 has an outer shell or jacket 119 that is threaded at one end 120 and includes a radial outer flange 121. The vial receiving station 117 of the transfer device is internally threaded to receive the threaded end of the vial jacket 119. Insertion and rotation of the vial jacket 119 forces an access spike 122 through the septum 106 of the vial. Continued rotation of the vial jacket causes the radial flange 121 to engage against a pushing member 123 located against the closed end of the pressurized gas cylinder 100. With additional rotation of the vial jacket, as best seen in FIG. 19, the pushing member 123 pushes the cylinder against piercing pin 124, causing it to pierce the seal cap of the cylinder and allowing gas to flow from the cylinder through flow passageways, not shown, through the access spike 122 (or a separate access spike) and into the vial 102 to force liquid medicament from the vial and into the injection device 103. The threaded connection between the transfer device receiving station and the vial jacket affords a mechanical advantage to the puncturing of the vial and the cylinder that may be beneficial to patients who have limited strength or dexterity.

As shown in FIGS. 18 and 19 there is a single access spike 122. In that situation, the spike will typically include two lumen or flow paths. One lumen will be for entry of gas and the other for outflow of liquid medicament. The outflow lumen may open in proximity to the inside surface of the septum, or at the lowest practical location when the vial is inverted, so that it is below the surface of the medicament and at a location so as to drain essentially all of valuable medicament from the vial. The gas entry lumen may open into the vial near the distal end of the spike 140, and spaced a substantial distance from the outflow lumen, so that substantially all the medicament flows from the vial before gas exits. The gas lumen may be configured open above the level of the medicament (when the vial is inverted) to enhance liquid transfer and reduce the risk of gas entrainment in the liquid. Alternatively, the gas inflow and liquid outflow lumen could be contained in separate spikes, particularly where the vial is pushed into the receiving station. In the threaded version of FIGS. 18 and 19, a single spike, with two lumen, would normally be used.

Figure 20:
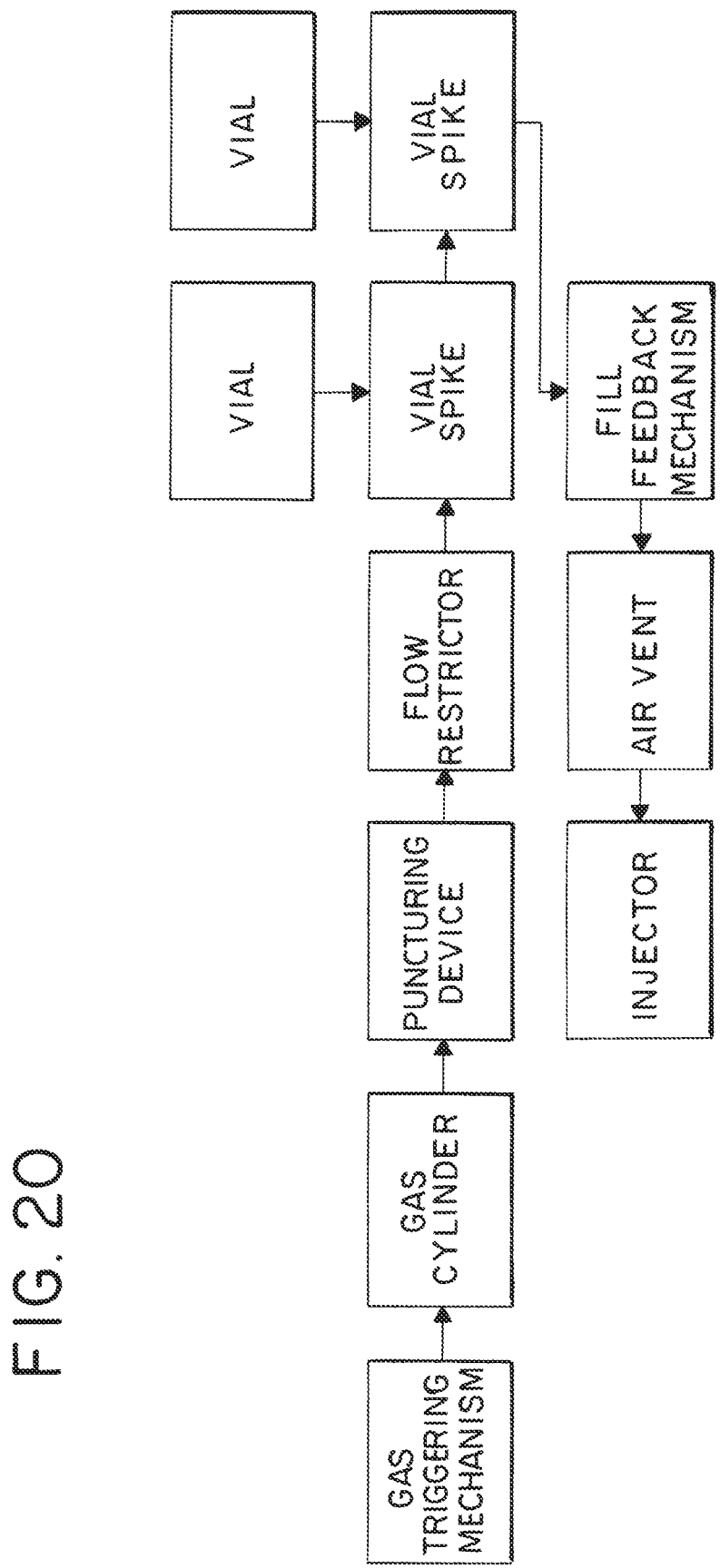
FIG. 20 is a flow chart of a method of pressurized gas-powered transfer and mixing of contents from two vials and transfer into an injection device in accordance with the present subject matter.

Turning now to FIG. 20. FIG. 20 is as flow chart, similar to FIG. 13, but in this case providing an overview of a dual vial fluid transfer method and some exemplary steps of the method using a pressurized gas source to power the transfer of contents, such as for example, diluent from a diluent vial into a medicament vial and combined diluent and medicament from the medicament vial, into an injection device. Alternatively, as noted earlier, a pressurized gas source may be used to power the transfer of medicament from a first liquid medicament vial into a second liquid medicament vial and the combined medicaments from the second vial into an injection device. Or, one of the vials may contain a diluent and the other vial contain concentrated liquid medicament. Other variations may also be employed.

Every step in FIG. 20 may not be required in all embodiments. As reflected in the flow chart, a vial containing medicament and a vial containing diluent are inserted into a vial receiving station of a transfer device, with a separate spike for piercing the vial septum and accessing the contents of each vial. Each spike may have two lumen, one for entering gas and another for outflow of diluent or medicament, or two separate spikes may be used for each vial.

The method is initiated by the user, as in the single vial process, by actuating a gas triggering mechanism which may be of various different configurations. As explained, the triggering mechanism may be actuated upon insertion of a vial into the vial receiving station or thereafter. Similar to the single vial system explained above, vial insertion may release a spring force that forces a piercing or puncturing pin through a sealing diaphragm or cap associated with a pre-filled pressure cylinder or cartridge-either by moving the puncturing pin or the pressure cylinder or both. Alternatively, the user's own force when inserting the vial into the receiving station may be employed to force a pre-filled gas cylinder and piercing pin together to access the pressurized gas. These are only a couple of non-limiting examples.

The pre-filled pressurized gas cartridge or cylinder, the gas itself, the flow restrictor and/or pressure regulator are generally as described above in connection with FIG. 13, although the pressurized gas cylinder used in a dual vial system may need to be of larger capacity and/or higher pressure than in the single vial system.

In the dual vial system, the pressurized gas is typically first directed into the first vial, such as a liquid medicament or a diluent-containing vial, and the pressure of the gas forces the liquid medicament or diluent from the first vial into a second or medicament vial. As noted in the introduction, the medicament may be a powder or in lyophilized form, and injection of the diluent is required to re-suspend or reconstitute the medicament. Both vials could also contain liquid medicaments or diluent and liquid medicament. The force of the pressurized gas also forces the resulting fluid, such as re-suspended medicament, from the second or medicament vial and into the injection device. A feedback mechanism may be provided to indicate when the contents of the medicament vial have been fully transferred to the injection device, and a vent may exhaust surplus gas to the ambient atmosphere. Because the volume of the pre-filled cylinder is small, the venting gas into the atmosphere will be relatively de minimus and may not even be noticeable to the user. As noted above, each vial could contain a liquid medicament, with a mixture or "cocktail" of the two medicaments, e.g., drugs, forced into the injection device.

After transfer to the injection device is completed, the injection device may be removed from the transfer device and used in the manner previously described in the published PCT application identified above.

Figure 21:
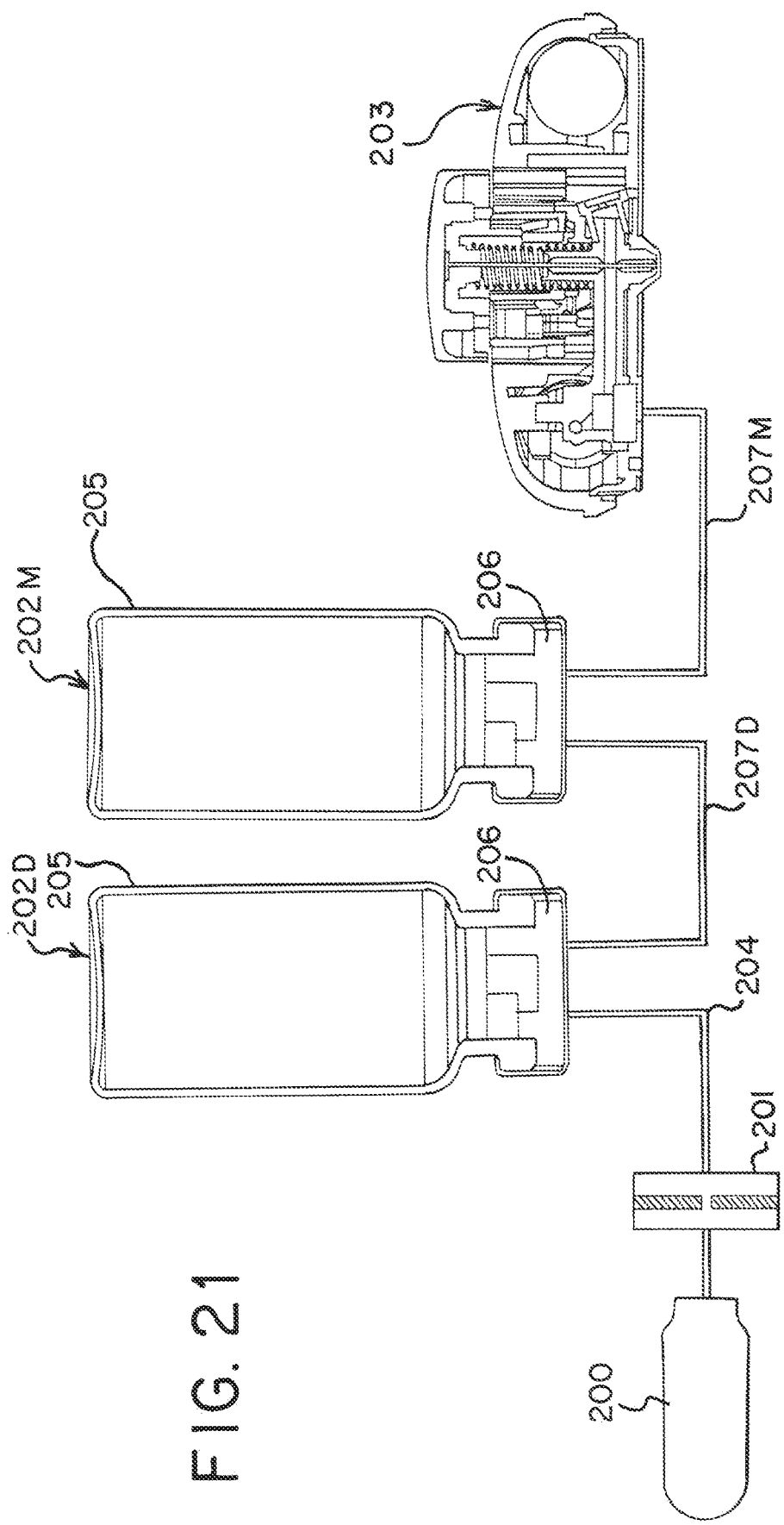
FIG. 21 is a flow diagram of a method of pressurized gas transfer and mixing of contents from two vials and transfer into an injection device in accorda.

For purposes of illustration and not limitation, FIG. 21 is a diagrammatic view of a pressurized gas powered dual vial re-suspension and transfer system, including a pressure vessel in the form of a prefilled pressurized gas cylinder or cartridge 200, a flow restrictor and/or pressure regulator 201, a liquid diluent vial 202D, a medicament vial 202M and an injection device 203. (Each vial 202D and 202M could also contain liquid medicament). The gas cylinder may be any suitable cylinder commercially available or may be a custom cylinder, as previously explained in connection with the single vial system.

Also similar to the single vial system, the gas may be any suitable gas, such as, but not exclusively, an inert gas preferably pathogen free—i.e., free of active pathogens. When released, such as by puncture by a piercing pin, the gas is directed through a suitable flowpath from the cylinder through the flow restrictor and/or pressure regulator 201 into the diluent vial 202D.

The flow restrictor and/or pressure regulator 201 may be of any suitable design, preferably small and disposable. A typical flow restrictor may be a diaphragm with a small orifice to limit the flow rate of gas from the cylinder. If desired, a pressure regulator may also be included in combination with or separate from the restrictor. From the restrictor/regulator, the flow path 204 conducts the gas to the diluent vial 202D.

The diluent (or first liquid medicament) vial 202D and medicament (or second liquid medicament) vial 202M may each be of standard drug vial configuration with a rigid container portion 205 usually glass, open at one end and sealed by a piercable diaphragm or septum 206 of latex, silicone or other material. The present process is preferably carried out with the vials in inverted vertical position so that the gas flows to the closed end of the vials, forcing essentially all the diluent and/or medicament from the vials under the force of the pressurized gas, before any gas exits the medicament vial.

From the diluent (or first liquid medicament) vial 202D, flow path 207D directs the diluent (or liquid medicament) under the pressure of the gas into the medicament vial 202M, where it may re-suspend the medicament if in a dry or lyophilized form or dilute the medicament if in liquid concentrated form (or simply combine or mix with the medicament if in liquid non-concentrated form). From the medicament vial 202M, combined medicament and diluent or diluted or mixed liquid medicament flows through flow path 207M under the pressure of the gas to any suitable vessel, such as an injection device 203 as disclosed in the previously identified PCT application. As pointed out above, the injection device may have an expandable reservoir, such as an elastomeric bladder, for receiving the medicament.

Figure 22:
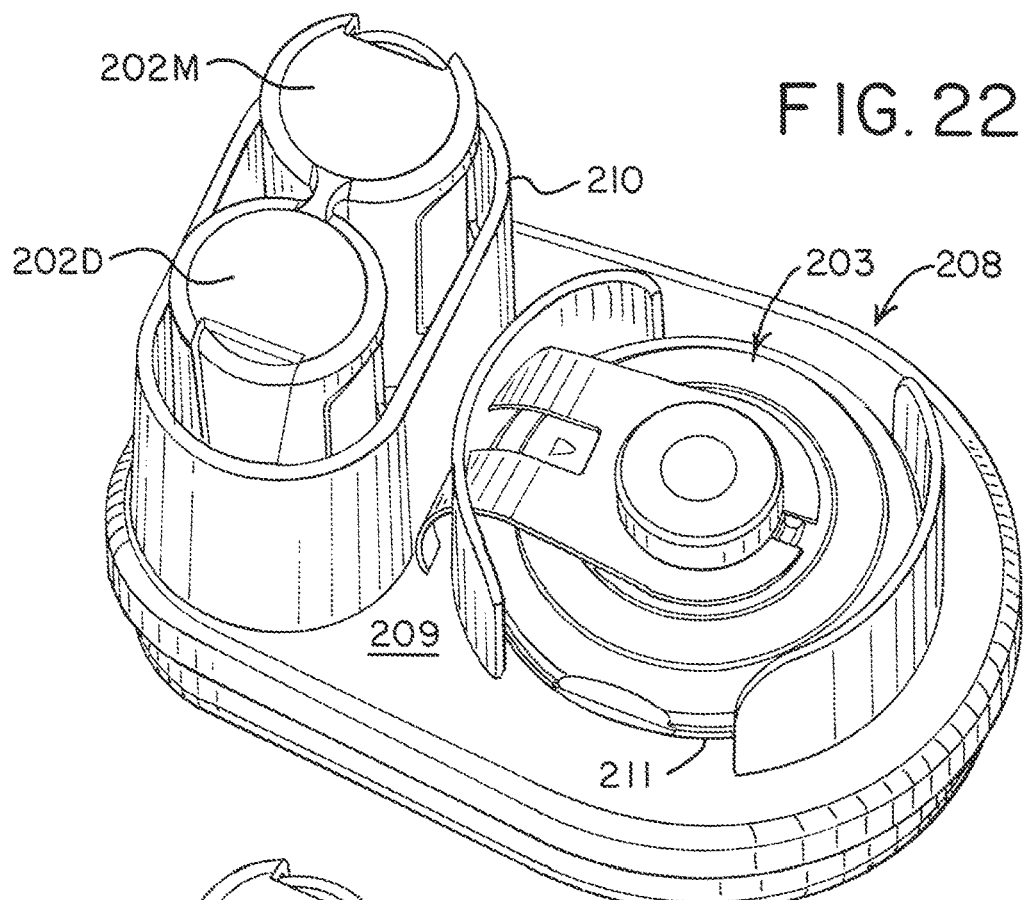
FIG. 22 is a perspective view of a dual vial transfer device embodying one aspect of the present subject matter.

FIG. 22 illustrates one potential transfer device, generally at 208, for effecting the transfer of liquid diluent or medicament from vial 202D to medicament vial 202M and from the medicament vial 202M into an injection device 203. The illustrated transfer device has a rigid plastic housing 209 that includes a dual vial receiving station 210, shown with vials 202D and 202M inserted, and an injection device receiving station 211, shown with the injection device 203 in place. The housing contains the fluid flow paths and operative mechanisms for effecting the transfer of diluent or medicament and resultant medicament to the injection device from the vials.

Figure 23:
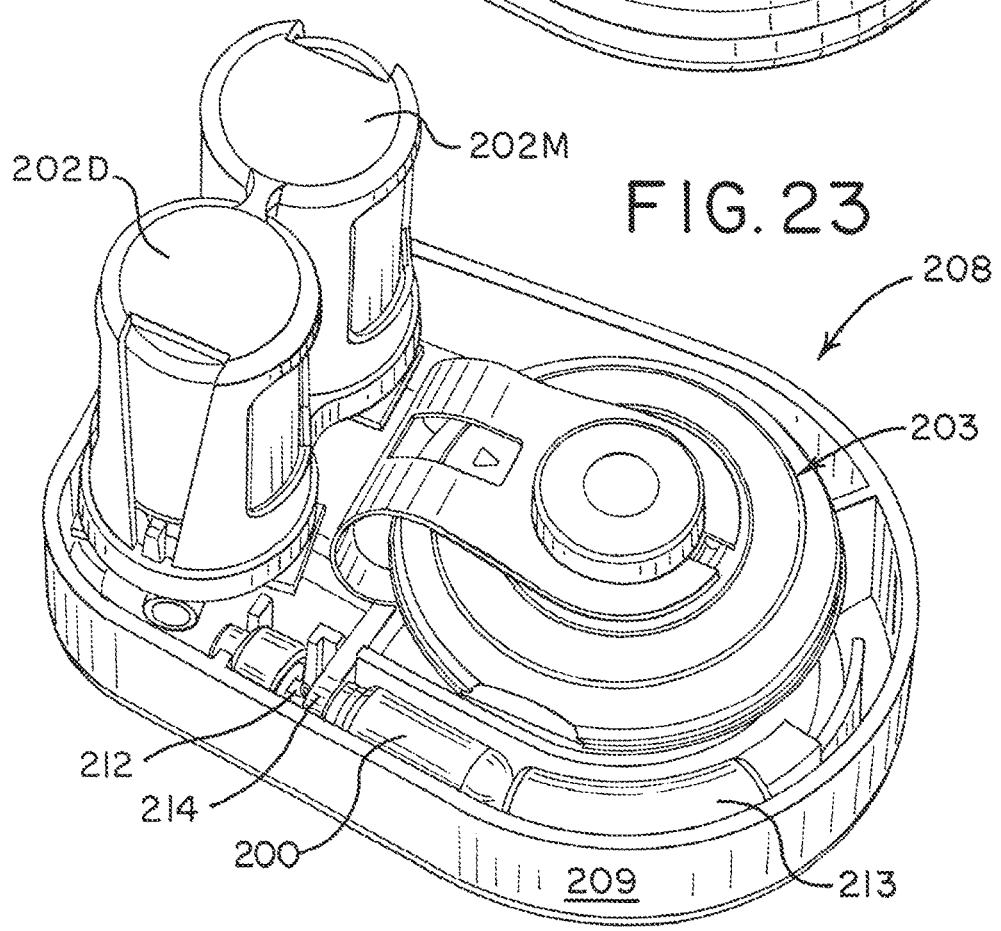
FIG. 23 is a perspective view of the device of FIG. 22, with a housing portion removed for better view of the interior.

This may be better seen in FIG. 23, which is similar to FIG. 22, but with the upper part of the housing 209 removed to allow view of certain of the inner parts. The fluid flow paths, which may be of suitable configuration, such as plastic tubing, are not visible in FIG. 23. With the removal of part of the housing in FIG. 23, the gas cylinder or cartridge 200 may be seen in a position before the gas is released by a piercing pin 212. In this position, the cylinder is positioned between a compressed spring, generally seen as member 213, and the pivotable or slidable latch or lever 214 which normally blocks movement of the gas cylinder toward the piercing pin.

Insertion of the vial pair 202D and 202M into the vial receiving station 210 simultaneously forces one or more access spikes (not seen in FIG. 23) through the vial septum of each vial and depresses the latch 214. When latch 214 is depressed, it moves to a non-blocking position, releasing the pressurized gas cylinder 200 for movement against the piercing pin 212 under the force of compressed coil spring 213, causing the pin to pierce a puncture area or sealing cap on the pressure cylinder and allowing the compressed gas to flow from the cylinder. Although described with the spring forcing the cylinder against the spike, alternatively the spike could be moved against the cylinder, and other types of force-generating devices other than coil springs could be utilized. If desired, both the spike and cylinder could be moved toward one another by the same or different force-generating devices.

Figure 24:
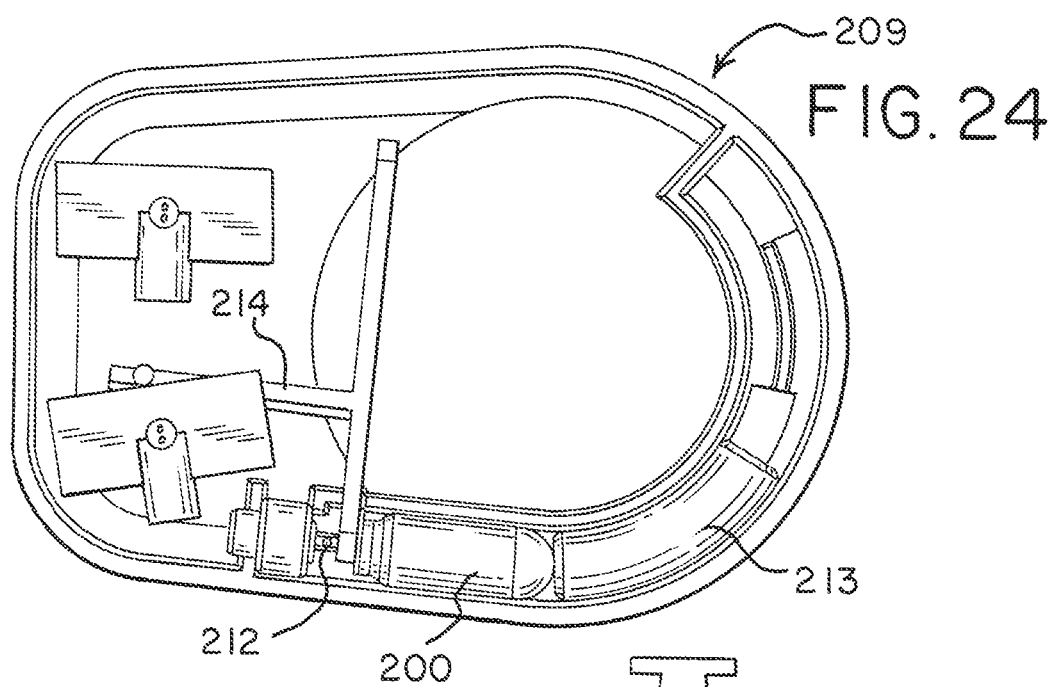
FIG. 24 is a horizontal cross-sectional view of the device of FIG. 22.

FIG. 24 is a top view of the lower portion of housing 214, with the vials 202D and 202M and injection device 203 removed to better illustrate the respective positions of the pressure cylinder 200, spring 213 and latch 214. The position shown is with the latch blocking movement of the cylinder and prior to puncture of the pressurized gas cylinder by the piercing pin 212.

Figure 25:
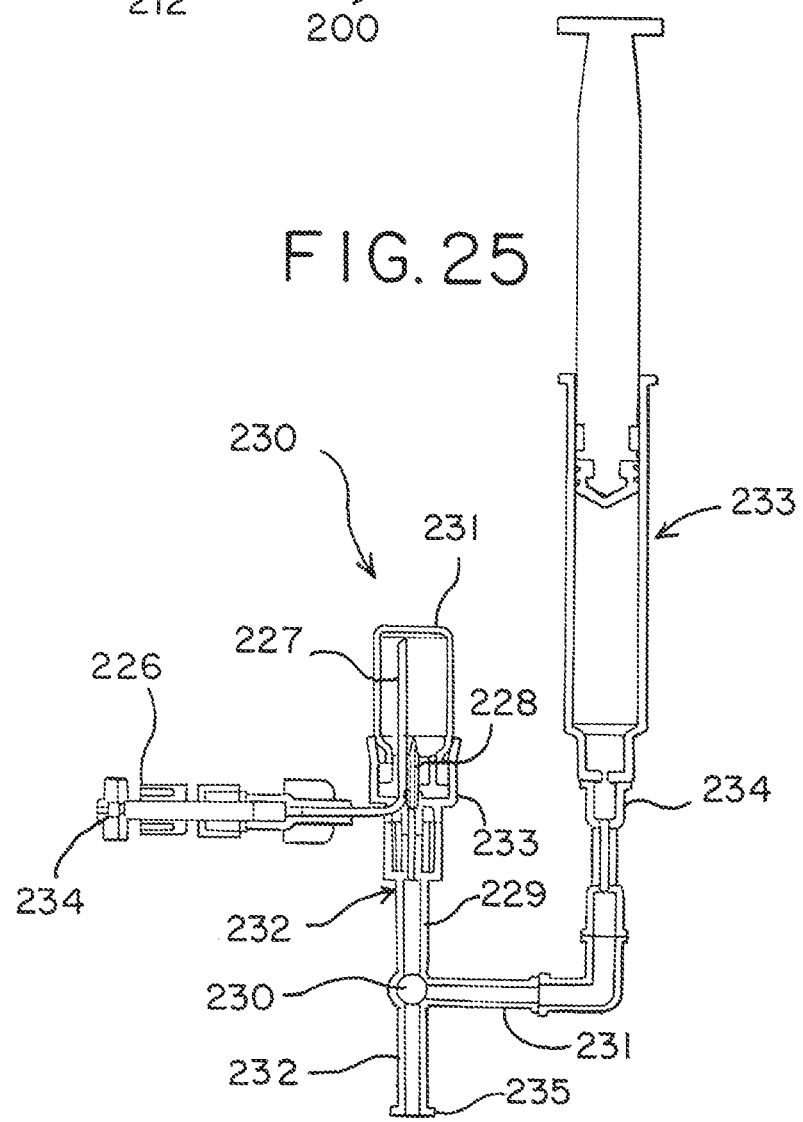
FIG. 25 is a cross-sectional view of another system/device useful for the re-suspension of medicament for injection.

FIG. 25 is a cross-sectional view of a system 230 for re-suspending a dry or micro-aggregate material stored in a container such as vial 231. The components of the system shown in FIG. 25 are exemplary only and may be varied as will be apparent after reading this description. In the illustrated embodiment, the system includes a housing, generally at 232 that has a vial receiving station 233, a diluent receiving port 234, a gas connection port 235 and vent port 226.

The illustrated vial receiving station 233 has two piercing spikes 227 and 228 for penetrating the septum of vial 231. Spike 227 extends substantially into the vial so as to open near the bottom of the vial and spaced from the vial septum, when it is inverted in a vertical position. Spike 228 is shorter and opens into the vial at a location in proximity to the inside surface of the septum. Each spike has a lumen. The lumen of spike 227 communicates, via tubing or other flow path in the housing 232, with the vent port 226. The lumen of spike 228 communicates with a flow path 229 that extends between the spike and one port on 3-way valve 230. Flow path 231 extends between another port on the 3-way valve and the diluent port 234, and flow path 232 extends between a third port on the three-way valve and gas port 235. Alternatively, a single piercing spike with dual lumen could also be used.

In the illustrated system, a syringe 233 is attached to the diluent port 234. The syringe can provide a source of diluent for re-suspension of the micro-aggregate in the vial and a means for later withdrawal of the suspension from the vial. In addition, a filter 234 is attached to the vent port 226. The filter may take any suitable form and is preferably hydrophobic to prevent liquid from escaping into the environment, as will be described below.

In operation, the vial 231 containing a dry material such as a medicament in micro-aggregate form is first attached to the vial receiving station 233. A diluent containing syringe 233 is attached to the diluent port 234, and a pressurized gas source (not shown) is attached to gas port 235. The three-way valve is set for the diluent to flow from flow path 231 into the fluid flow path 229 leading to spike 228. The diluent is injected from the syringe into the vial. The valve 230 is then turned so that gas can flow from the gas port 235, through passageway 229 into the spike 228. The spike 228 opens into the vial below the level of the diluent and the bubbling gas entering the vial causes agitation between the diluent and micro-aggregate material. The gas rises to the bottom of the inverted vial and exits through the lumen of spike 227. In the event that the gas carries any liquid with it, the hydrophobic filter 234 in the vent flow path prevents the escape of the liquid while allowing the gas to continue to vent.

The introduction of gas into the vial continues for a selected period of time until the micro-aggregate is substantially fully suspended in the diluent due to the agitation of the entering gas. The 3-way valve is then returned to the position where the diluent flow path 231 and flow path 229 are in communication, and the syringe 233 is retracted to withdraw the suspended micro-aggregate from the vial. The filter 234 allows displacement air to vent into the vial, and the position of spike 228 allows substantially all of the micro-aggregate to be withdrawn from the vial. With this system, the micro-aggregate can be reliably and predictably re-suspended without concern for the uncertainty and variability that can occur when manual re-suspension is employed.

Additional Aspects and Variations

Without limiting any of the foregoing or the attached claims, other general and more specific aspects and variations of the subject matter of this description are set forth below.

Aspect 1 is a method of transferring fluid from a fluid-containing vial to an injection device comprising: introducing pressurized gas into a vial; flowing fluid from the vial under pressure from the gas; and flowing the fluid from the vial into an injection device under the force of the pressurized gas.

Aspect 2 is the method of aspect 1 in which the fluid is a diluent and the pressurized gas is flowed into the diluent-containing vial and diluent is flowed from the diluent-containing vial into a medicament-containing vial and combined diluent and medicament is flowed from the medicament-containing vial into the injection device under pressure from the pressurized gas.

Aspect 3 is the method of aspect 1 in which the vial is a first vial containing a first liquid medicament and the first medicament is flowed from the first vial into a second vial containing a second liquid medicament, and mixed first and second medicaments are flowed from the second vial into an injection device under the force of the pressurized gas.

Aspect 4 is the method of aspect 1, 2 or 3 in which the injection device includes an expandable reservoir, and the fluid or the combined diluent and medicament or the mixed first and second medicaments is flowed into the expandable reservoir under pressure from the pressurized gas.

Aspect 5 is the method of aspect 3 in which the expandable reservoir comprises an elastomeric bladder.

Aspect 6 is the method of aspect 3 or 4 in which the reservoir is biased to expel the fluid or combined diluent and medicament or mixed first and second medicaments.

Aspect 7 is the method of any one of aspects 1-6 in which the pressurized gas is flowed from a pre-filled pressure vessel.

Aspect 8 is the method of aspect 7 in which the vessel includes a puncturable seal and the method includes puncturing the seal.

Aspect 9 is the method of any one of aspects 1-8 in which the gas is essentially pathogen free.

Aspect 10 is the method of any one aspects 1-9 including filtering the gas before it enters a vial.

Aspect 11 is the method of any one of aspects 7-10 in which the pressure vessel is a gas-filled cartridge having a volume of 10 ml or less.

Aspect 12 is the method of aspect 11 in which the cartridge has volume of about 1 ml or less.

Aspect 13 is the method of any one of aspects 7-12 in which the pressure vessel initially contains gas at a pressure of greater than about 500 psig.

Aspect 14 is the method of any one of aspects 1-13 in which the gas is an inert gas.

Aspect 15 is the method of any one of aspects 1-14 in which the gas is selected from the group consisting of nitrogen, helium, neon, argon, krypton, and xenon.

Aspect 16 is the method of any one of aspects 4-16 including removing entrained gas from the fluid before it enters the expandable reservoir.

Aspect 17 is the method of any one of aspects 1-16 in which the pressurized gas is flowed from a pre-filled cartridge having a volume of about 1 ml or less and a pressure of about 900 psig or greater.

Aspect 18 is the method of any one of aspects 1-17 including controlling the flow rate and/or pressure of gas.

Aspect 19 is medicament transfer apparatus for transferring fluid from a fluid-containing vial to an injection device, comprising a pressurized gas source, at least one vial receiving station, and a medication injection device receiving station, a gas flow path communicable between the gas source and the vial receiving station and a fluid flow path communicable between the vial receiving station and the medication injection device receiving station.

Aspect 20 is the medicament transfer apparatus of aspect 19 in which transfer apparatus includes at least a first vial receiving station and a second vial receiving station and the gas flow path is communicable between the pressurized gas source and the first vial receiving station and the fluid flow path is communicable between the first vial receiving station and the second vial receiving station and between the second vial or final receiving station and the injection device.

Aspect 21 is the medicament transfer apparatus of aspect 19 or 20 in which the pressurized gas source comprises a pre-filled pressure vessel.

Aspect 22 is the medicament transfer apparatus of aspect 21 in which the vessel includes a puncturable seal and the apparatus includes a puncturing pin for puncturing the seal.

Aspect 23 is the medicament transfer apparatus of aspect 21 including an actuator for moving the puncturing pin and/or the pressure vessel between a pre-puncture position and a puncture position.

Aspect 24 is the medicament transfer apparatus of aspect 22 in which the actuator comprises a stored energy source biased to move the puncturing pin and/or the pressure vessel to the puncture position.

Aspect 25 is the medicament transfer apparatus of aspect 23 in which the stored energy device comprises a spring.

Aspect 26 is the medicament transfer apparatus of aspect 21 in which the puncturing pin includes a seal for contacting the pressure vessel to limit the escape of pressurized gas into the ambient environment.

Aspect 27 is the medicament transfer apparatus of any one of aspects 19-26 in which the pressurized gas is essentially pathogen free.

Aspect 28 is the medicament transfer apparatus of any one of aspects 19-27 in which the gas flow path includes a filter for filtering the gas before it enters a vial.

Aspect 29 is the medicament transfer apparatus of any one of aspects 19-28 in which the pressurized gas source is a pre-filled gas cartridge having a volume of 10 ml or less.

Aspect 30 is the medicament transfer apparatus of any one of aspects 19-29 in which the pressurized gas source has volume of about 1 ml or less.

Aspect 31 is the medicament transfer apparatus of any one of aspects 19-30 in which the pressure source initially contains gas at a pressure greater than about 500 psig.

Aspect 32 is the medicament transfer apparatus of any one of aspects 19-31 in which the gas is an inert gas.

Aspect 33 is the medicament transfer apparatus of any one of aspects 19-31 in which the gas is selected from the group consisting of nitrogen, helium, neon, argon, krypton, and xenon.

Aspect 34 is the medicament transfer apparatus of any one of aspects 19-32 in which the fluid flow path includes a gas trap for removing entrained gas from the fluid before it enters the injection device.

Aspect 35 is the medicament transfer apparatus of any one of aspects 19-32 in which the pressurized gas source is a pre-filled cartridge having a volume of about 1 ml or less and a pressure of about 900 psig or greater.

Aspect 36 is the medicament transfer apparatus of any one of aspects 19-35 including a flow regulator and/or pressure regulator for controlling the flow rate and/or pressure of gas from the pressurized gas source.

Aspect 37 is the medicament transfer apparatus of any one of aspects 19-36 including a medicament injection device received in the injection device receiving station.

Aspect 38 is the medicament transfer apparatus of aspect 37 in which the injection device includes a reservoir that is expandable under pressure of fluid or combined diluent and medicament or mixed medicament flow under the force of pressurized gas.

Aspect 39 is the medicament transfer apparatus of aspect 38 in which the expandable reservoir comprises an elastomeric bladder.

Aspect 40 is the medicament transfer apparatus of aspect 38 or 39 in which the expandable reservoir is biased when expanded to expel the fluid or combined diluent and medicament or mixed medicament.

Aspect 41 is a re-suspension device for re-suspending medicament contents of a vial of the type having an open end sealed by a septum, the re-suspension device comprising: a housing including; a diluent port; a gas port; a vent port; a vial receiving station; a first spike lumen and a second spike lumen extending from the vial receiving station for piercing a vial septum when a vial is received at the vial receiving station; a gas flow path communicating between the gas entry port and the first spike lumen; a diluent flow path communicating between the diluent port and the first spike lumen; a vent flow path communicating between the vent port and the second spike lumen; and a hydrophobic filter cooperatively associated with the vent flow path for filtering gas passing the vent flow path and substantially preventing the escape of liquid from the vent flow path.

Aspect 42 is the re-suspension device of aspect 41 comprising a flow junction between the gas flow path and the diluent flow path upstream of the first spike lumen and a valve associated with the flow junction to control flow of gas and/or diluent, respectively, between the first spike lumen and the gas port and the first spike lumen and the diluent port.

Aspect 43 is the re-suspension device of aspect 41 or 42 in which the first spike lumen and second spike lumen are defined in a single piercing spike.

Aspect 44 is the re-suspension device of aspect 41 in which the first spike lumen is defined in a first piercing spike and the second spike lumen is defined in a separate second piercing spike.

Aspect 45 is the re-suspension device any one of aspects 41-44 in which the second spike lumen has a greater length than the first spike lumen so as to extend farther into a vial received at the receiving station.

Aspect 46 is the re-suspension device of any one of aspects 41-45 in which the first spike lumen is configured to open into a vial so as to be below the level of diluent during re-suspension and the second spike lumen is configured to open into the vial at a location so as to be above the level of diluent during re-suspension.

Aspect 47 is the re-suspension device of any one of aspects 41-46 in which the first spike lumen is configured to open into a vial at a location proximal to the septum and the second spike lumen is configured to open into the vial at a location substantially spaced from the septum.

Aspect 48 is a method of re-suspending medicament contents of a vial, the method comprising: introducing diluent into the vial; injecting gas under pressure into the vial below the level of the diluent in the vial to cause agitation of the diluent; venting gas from the vial; and continuing the injecting and venting until the medical contents are substantially resuspended.

Aspect 49 is the method of re-suspending of aspect 48 including substantially preventing the escape of liquid with the venting gas.

Aspect 50 is the method of re-suspending of aspect 48 or 49 in which the venting gas is passed through a hydrophobic filter to substantially prevent the escape of liquid from the vial.

Aspect 51 is the method of any one of aspects 48-50 in which gas is vented from the vial at a level above the level of diluent.

Aspect 52 is the method of any one of aspects 48-51 in which the medicament contents of the vial are substantially in a dry state.

Aspect 53 is the method of any one of aspects 48-52 in which the medicament contents of the vial comprise a lyophilized material.

Aspect 54 is the method of any one of aspects 48-53 in which the gas is substantially free of pathogens.

Although the present subject matter has been described with reference to the illustrated examples and various aspects and variations, this is only purposes of explanation and not limitation. It is understood that the present subject matter may have application in other circumstances or may be varied in detail without departing from the disclosure herein.

The invention claimed is:

1. A medicament transfer apparatus for transferring fluid from a fluid-containing vial to an injection device, comprising:
a pressurized gas source comprising a pre-filled pressure vessel including a puncturable seal,
at least one vial receiving station including a gas lumen and a liquid lumen, and a medication injection device receiving station, a gas flow path communicable between the gas source and the gas lumen of the at least one vial receiving station and a fluid flow path communicable between the liquid lumen of the at least one vial receiving station and the medication injection device receiving station,
a puncturing pin for puncturing the puncturable seal,
an actuator for moving the puncturing pin and/or the pre-filled pressure vessel between a pre-puncture position and a puncture position;
said at least one vial receiving station configured so that a vial received therein is movable from a first position to a second position, wherein the gas lumen and the liquid lumen come into fluid communication with an interior of the vial when the vial is moved into the second position; and
said actuator including a member that is operatively engaged when the vial in said at least one is moved into the second position whereby the puncturing pin and/or the pre-filled pressure vessel is moved into the puncture position.

2. The medicament transfer apparatus of claim 1 in which the actuator comprises a stored energy source biased to move the puncturing pin and/or the pre-filled pressure vessel to the puncture position.

3. The medicament transfer apparatus of claim 2 in which the stored energy device comprises a spring.

4. The medicament transfer apparatus of claim 1 further comprising a spike containing the gas lumen and the liquid lumen, said spike configured to pass through a septum of the vial positioned in the at least one vial receiving station as the vial is moved from the first position to the second position.

5. The medicament transfer apparatus of claim 1 further comprising a first spike containing the gas lumen and a second spike containing the liquid lumen, said first and second spikes configured to pass through a septum of the vial positioned in the at least one vial receiving station as the vial is moved from the first position to the second position.

6. The medicament transfer apparatus of claim 1 wherein the medication injection device receiving station is configured to support a medication injection device as a liquid medicament is transferred to the medication injection device via the fluid flow path.

* * * * *